US012642627B2

(12) United States Patent
Srouji

(10) Patent No.: US 12,642,627 B2
(45) Date of Patent: Jun. 2, 2026

(54) DEVICE AND METHOD FOR TREATMENT OF AN ARTIFICIAL BONE IMPLANT WITH BLOOD

(71) Applicant: HEALTH CORPORATION OF GALILEE MEDICAL CENTER, Nahariya (IL)

(72) Inventor: Samer Srouji, Haifa (IL)

(73) Assignee: HEALTH CORPORATION OF GALILEE MEDICAL CENTER, Nahariya (IL)

( * ) Notice: Subject to any disclaimer, the term of this patent is extended or adjusted under 35 U.S.C. 154(b) by 10 days.

(21) Appl. No.: 18/999,585

(22) Filed: Dec. 23, 2024

(65) Prior Publication Data

US 2025/0169926 A1     May 29, 2025

Related U.S. Application Data

(62) Division of application No. 17/182,710, filed on Feb. 23, 2021, now Pat. No. 12,201,496, which is a
(Continued)

(51) Int. Cl.
  *A61C 8/00*        (2006.01)
  *A61B 5/15*        (2006.01)
  (Continued)

(52) U.S. Cl.
  CPC .............. *A61C 8/0087* (2013.01); *A61C 5/70* (2017.02); *A61C 8/0006* (2013.01); *A61F 2/28* (2013.01); *A61F 2/30767* (2013.01); *A61L 27/3608* (2013.01); *A61L 27/3616* (2013.01);

*A61L 27/3691* (2013.01); *A61L 27/54* (2013.01); *A61B 5/150099* (2013.01); *A61C 8/0013* (2013.01); *A61F 2002/2817* (2013.01); *A61F 2002/3093* (2013.01); *A61F 2/4644* (2013.01); *A61L 2300/30* (2013.01);
(Continued)

(58) Field of Classification Search
None
See application file for complete search history.

(56)        References Cited

U.S. PATENT DOCUMENTS 3,706,306  A      12/1972  Berger et al.
4,856,648  A       8/1989  Krueger
              (Continued)

FOREIGN PATENT DOCUMENTS

CN        203724605 U      7/2014
EP           2644208 A1    10/2013
WO       2005004755 A1     1/2005

*Primary Examiner* — Alexander M Weddle
(74) *Attorney, Agent, or Firm* — William H. Dippert; Lawrence A. Greenberg; Werner H. Stemer

(57)        ABSTRACT

A method for treating an artificial bone implant with blood, according to the method bone material is placed in a container configured to be filled with blood, wherein the container comprises an opening and a cover configured to cover the opening of the container and a fixed separator that separates a bottom part and an upper part. The separator is provided with holes so that when the container is filled with whole blood, the blood in the bottom part is in full contact with the blood in the upper part, and wherein the bone material is in the upper part, on top of the separator.

3 Claims, 21 Drawing Sheets

Related U.S. Application Data division of application No. 15/773,461, filed as application No. PCT/IL2016/051196 on Nov. 3, 2016, now abandoned.

(60) Provisional application No. 62/249,980, filed on Nov. 3, 2015.

(51) Int. Cl.

| | |
|---|---|
| *A61C 5/70* | (2017.01) |
| *A61C 8/02* | (2006.01) |
| *A61F 2/28* | (2006.01) |
| *A61F 2/30* | (2006.01) |
| *A61F 2/46* | (2006.01) |
| *A61L 27/36* | (2006.01) |
| *A61L 27/54* | (2006.01) |

(52) U.S. Cl.
CPC ..... *A61L 2300/412* (2013.01); *A61L 2420/02* (2013.01); *A61L 2430/02* (2013.01)

(56) References Cited

U.S. PATENT DOCUMENTS

| | | | |
|---|---|---|---|
| 5,062,800 | A | 11/1991 | Niznick |
| 5,368,160 | A | 11/1994 | Leuschen et al. |
| 5,622,500 | A | 4/1997 | Niznick |
| 5,755,575 | A | 5/1998 | Biggs |
| 6,086,371 | A | 7/2000 | Bassett et al. |
| 6,217,332 | B1 | 4/2001 | Kumar |
| 6,913,465 | B2 | 7/2005 | Howlett et al. |
| 9,283,074 | B2 | 3/2016 | Evans et al. |
| 9,782,518 | B2 | 10/2017 | Hotta et al. |
| 2001/0031445 | A1 | 10/2001 | Artal |
| 2004/0259972 | A1 | 12/2004 | Ringeisen et al. |
| 2005/0023166 | A1 | 2/2005 | Howlett et al. |
| 2011/0284399 | A1 | 11/2011 | Donley |
| 2013/0253657 | A1* | 9/2013 | Hotta ................. A61L 27/3616 427/2.24 |
| 2014/0166509 | A1 | 6/2014 | Chung et al. |
| 2016/0100889 | A1 | 4/2016 | Devouassoux et al. |

* cited by examiner

112 — Withdrawing blood from a patient

114 — Transferring the blood into a device containing an implant

116 — Centrifuging the device

118 — Removing the implant from the device

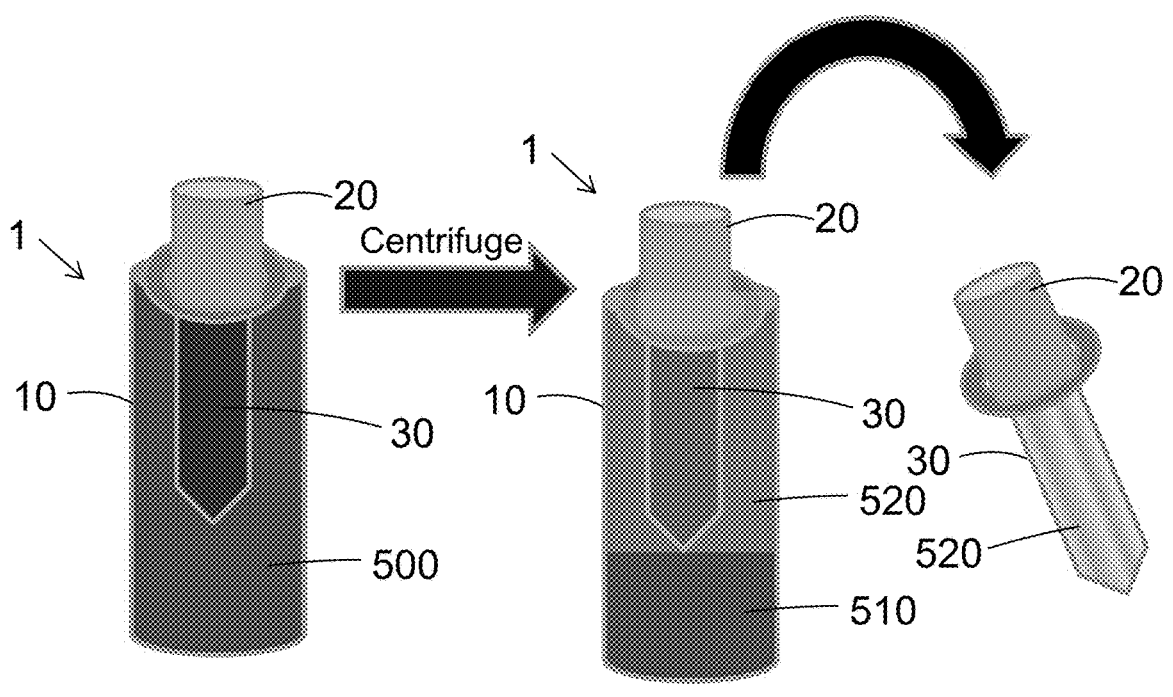
FIG. 5A                FIG. 5B                FIG. 5C
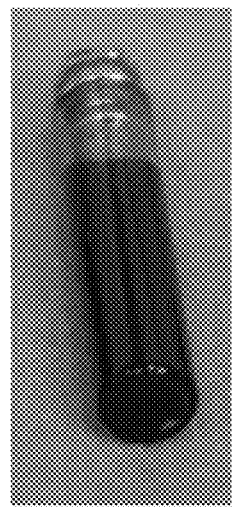 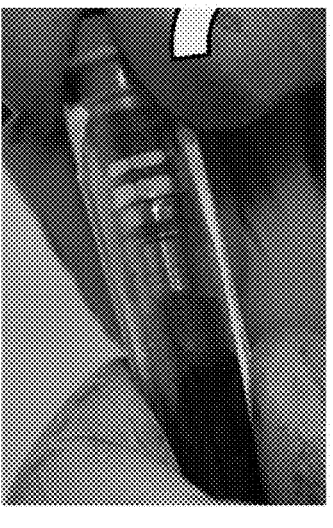 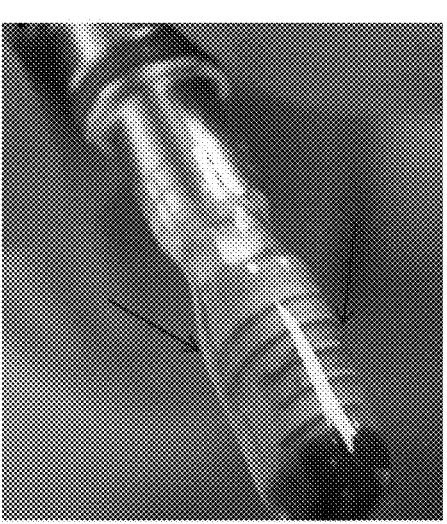
FIG. 6A          FIG. 6B          FIG. 6C

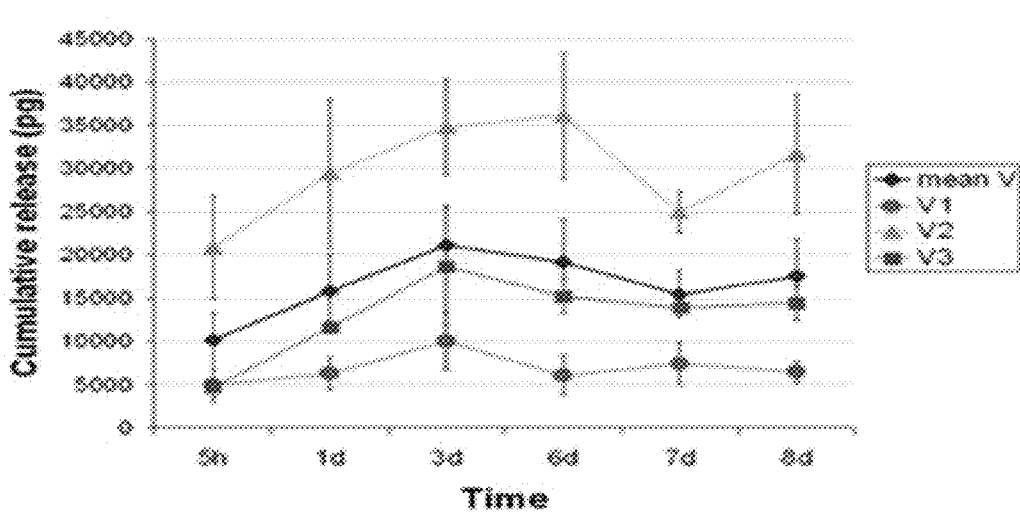
FIG. 9A
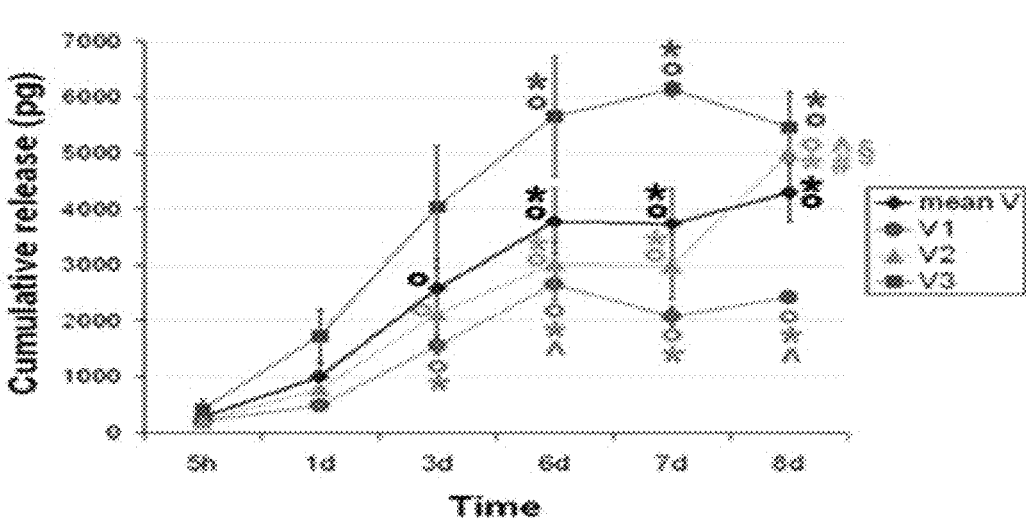
FIG. 9B

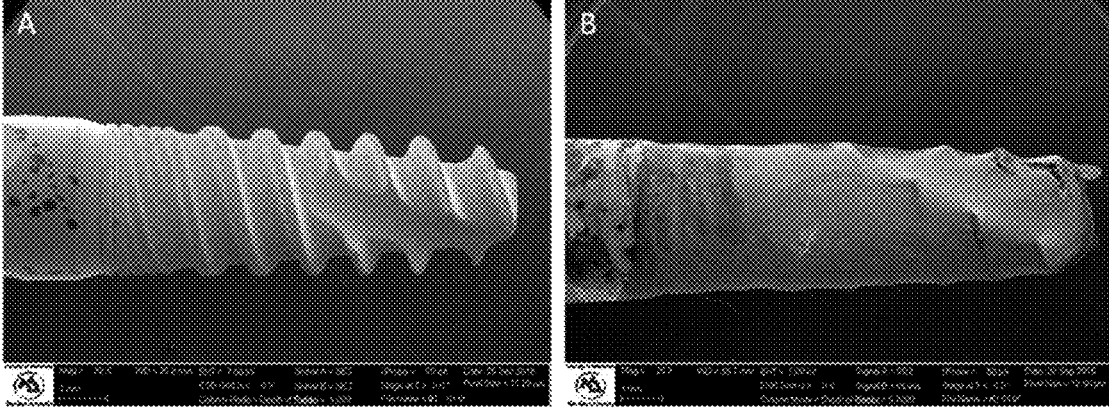
FIG. 10A                    FIG. 10B
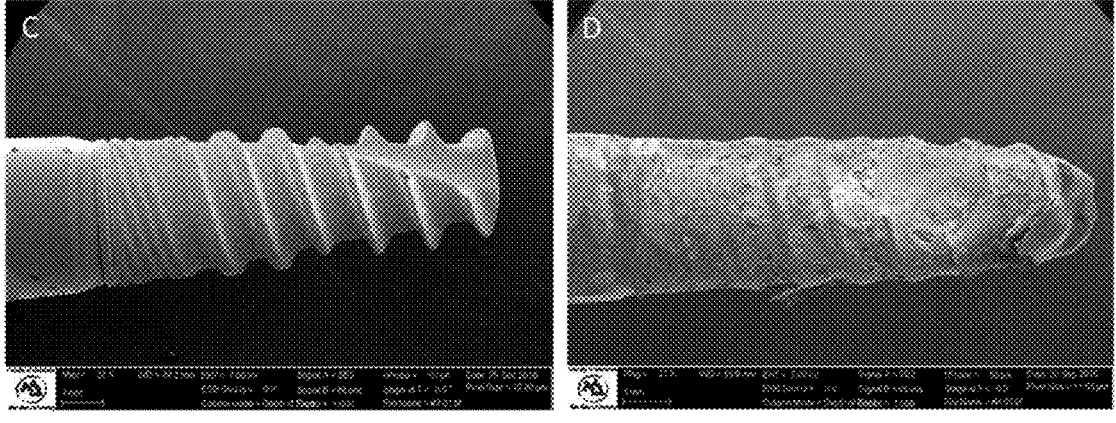
FIG. 10C                    FIG. 10D

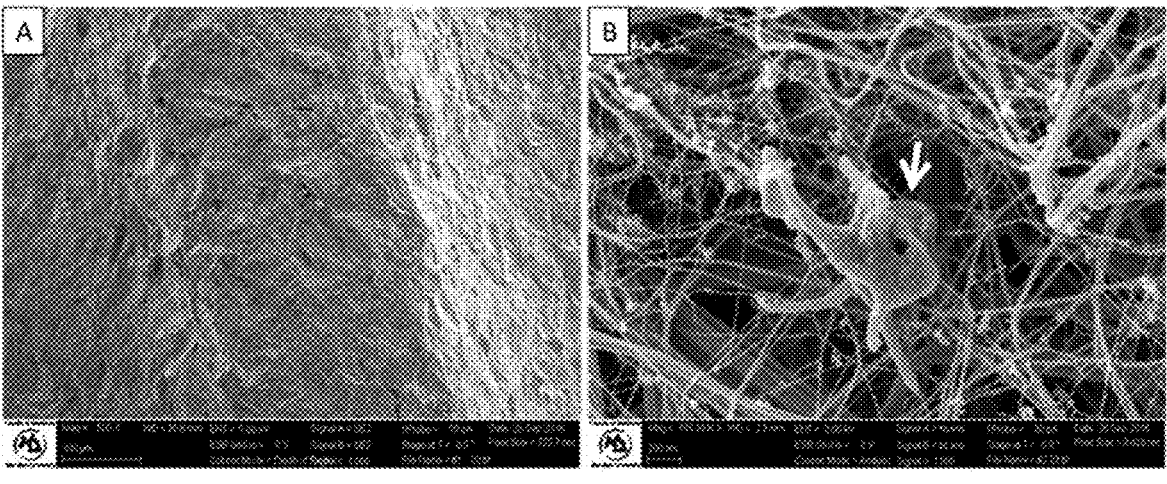
FIG. 11A                    FIG. 11B
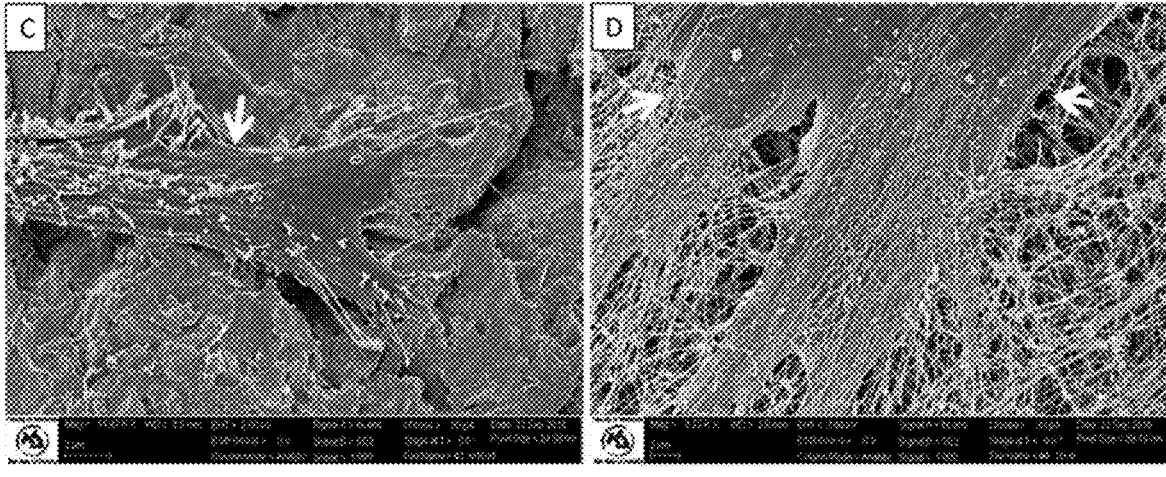
FIG. 11C                    FIG. 11D

DEVICE AND METHOD FOR TREATMENT OF AN ARTIFICIAL BONE IMPLANT WITH BLOOD

CROSS-REFERENCE TO RELATED APPLICATIONS

This application is a divisional of U.S. patent application Ser. No. 17/182,710, filed Feb. 23, 2021, now U.S. Pat. No. 12,201,496, which in turn is a divisional of U.S. patent application Ser. No. 15/773,461, filed May 3, 2018, now abandoned, which is in turn a National Phase filing under 35 U.S.C. § 371 of International Patent Application No. PCT/IL2016/051196, filed Nov. 3, 2016, which is based upon and claims the benefit of the priority date of U.S. Provisional Patent Application Ser. No. 62/249,980, filed Nov. 3, 2015, each of which is incorporated herein by reference.

FIELD OF THE INVENTION

The present subject matter relates to artificial bone implants. More particularly, the present subject matter relates to treatment of artificial bone implants before placing the artificial bone implants in a patient's body.

BACKGROUND OF THE INVENTION

Sometimes there is a need to treat artificial bone implants, for example dental implants and bone substitutes, with various types of preparations and substances in order to enhance rehabilitation of the tissue where the artificial bone implant is planted. Of particular interest is the treatment of artificial bone implants with preparations that promote accelerated osseointegration of the artificial bone implants.

Artificial bone implants are made of biocompatible materials. For example, dental implants are made of titanium. One of the processes that promote proper settlement of the artificial bone implant in a bone tissue is osseointegration, also known as osseointegration. Osseointegration is a direct structural and functional connection between a living bone and a surface of an artificial bone implant. In other words, osseointegration may be defined as formation of a direct interface between an artificial bone implant and bone, without intervening soft tissue. This is achieved by a structural linkage made at a contact point between a bone and a surface of an artificial bone implant.

Osseointegrated implants have been used to treat edentulism, and for head and neck reconstruction to facilitate retention of auricularmandibular, maxillary, nasal, and orbital implants, and for bone-anchored hearing aids.

Referring specifically to artificial dental implants, osseointegration is the main requirement for installed dental implant stability. Similar to traumatic insults to bony tissues, the drilling of an implant cavity leads to distinct phases comprising a cascade of complex physiological mechanisms similar to direct fracture healing. At first, fibrin polymerization and the formation of a blood clot occurs due to mechanisms of cellular and plasmatic hemostasis. The blood clot serves as an extracellular matrix supporting invading bone-forming cells and neoangiogenesis. Then, osteogenic cells generate new bone tissue within the borders of the drill hole, onto the surface of the installed implant. Osteoblasts migrate to the surface of the implant cavity, differentiate, and lead to the formation of new bone tissue in an appositional manner. The degree of new bone formation at the implant-drill hole interface largely dictates the stability of installed dental implants. After a three to six-month period remodeling phase, the dental implant surface is 60-70% covered by newly formed bone, which closely reflects the degree of osseointegration.

It is appreciated that acceleration of the osseointegration process of artificial bone implants is of importance, for example in order to shorten the recovery period after placing an artificial bone implant in a bone tissue. Of great importance is the acceleration of osseointegration of dental implants, as further steps are required following placing the dental implant, such as attachment of a dental prosthetic, for example a tooth, a bridge or a denture, to the implant, or placing an abutment that will hold a dental prosthetic. However, advance to these further steps depends on healing of the tissue surrounding the implant. Accelerated osseointegration of the dental implant shortens the healing time after placing the dental implant and expedites the entire process of dental implantation.

One way of accelerating osseointegration of an artificial bone implant, for example a dental implant, is covering the surface of the artificial bone implant with substances or preparations that promote osseointegration, for example growth factors. Furthermore, treating the artificial bone implant with additional types of materials or preparations is advantageous. Examples of such additional type of materials or preparations include, but not limited to, materials or preparations that affect healing of a surrounding tissue of an implant, enhance healing time after implantation, and improve the condition of a patient undergone implantation—for example antibiotic substances, pain relievers, and the like.

The currently available devices and methods for pre-treating artificial bone implants are cumbersome and time consuming.

Therefore, there is a need for a device and methods for pre-treating easily and shortly an artificial bone implant, for example a dental implant and bone substitute, before placement of the artificial bone implant in a target bone tissue.

SUMMARY OF THE INVENTION

Unless otherwise defined, all technical and scientific terms used herein have the same meaning as commonly understood by one of ordinary skill in the art to which this subject matter belongs. Although methods and materials similar or equivalent to those described herein can be used in the practice or testing of the present subject matter, suitable methods and materials are described below. In case of conflict, the patent specification, including definitions, will control. In addition, the materials, methods, and examples are illustrative only and not intended to be limiting.

According to one aspect of the present subject matter, there is provided a device for treating an artificial bone implant with blood, the device comprising: a container configured to accommodate an artificial bone implant and be filled with blood, wherein the container comprises an opening; and a cover configured to cover the opening of the container.

According to one embodiment, the device is configured to be centrifuged.

According to another embodiment, the container and the cover are configured to maintain a negative air pressure in the container compared to an ambient air pressure.

According to yet another embodiment, the cover is configured to attach to an artificial bone implant so that the artificial bone implant is held by the cover.

According to a further embodiment, the artificial bone implant is a dental implant.

According to yet a further embodiment, the container further comprises a separator separating the container to an upper part and a bottom part, wherein the separator comprises holes that allow contact of blood in the upper part with blood in the bottom part.

According to an additional embodiment, the artificial bone implant is a bone material.

According to yet an additional embodiment, the separator is configured to maintain the bone material in the upper part of the container.

According to another aspect of the present subject matter, there is provided a method for covering an artificial bone implant with osseointegration accelerators, the method comprising: withdrawing blood from a patient; transferring the blood into a device for treating an artificial bone implant with blood, wherein the device comprises a container configured to accommodate an artificial bone implant and be filled with blood, and wherein the container comprises an opening; and a cover configured to cover the opening of the container, and wherein the container contains the artificial bone implant; centrifuging the device; and removing the implant from the device.

According to one embodiment, the container and the cover are configured to maintain a negative air pressure in the container compared to an ambient air pressure, and the blood is transferred into the container due to a negative air pressure in the container.

According to another embodiment, after withdrawing the blood from the patient, the blood is centrifuged, and plasma separated from the centrifuged blood is transferred in to the device, and wherein instead of centrifuging the device, the plasma is allowed to coagulate.

According to yet another embodiment, the plasma is allowed to coagulate in an accelerated manner.

According to still another embodiment, the coagulation of the blood or plasma is accelerated by shaking, or ultra-sonication, or any combination thereof.

BRIEF DESCRIPTION OF THE DRAWINGS

Embodiments are herein described, by way of example only, with reference to the accompanying drawings. With specific reference now to the drawings in detail, it is stressed that the particulars shown are by way of example and for purposes of illustrative discussion of the preferred embodiments, and are presented in the cause of providing what is believed to be the most useful and readily understood description of the principles and conceptual aspects of the embodiments. In this regard, no attempt is made to show structural details in more detail than is necessary for a fundamental understanding, the description taken with the drawings making apparent to those skilled in the art how several forms may be embodied in practice.

In the drawings.

4 accelerators before implanting the artificial bone implant in a target bone tissue, using the device of the present subject matter.

Figures 4A, 4B, 4C:
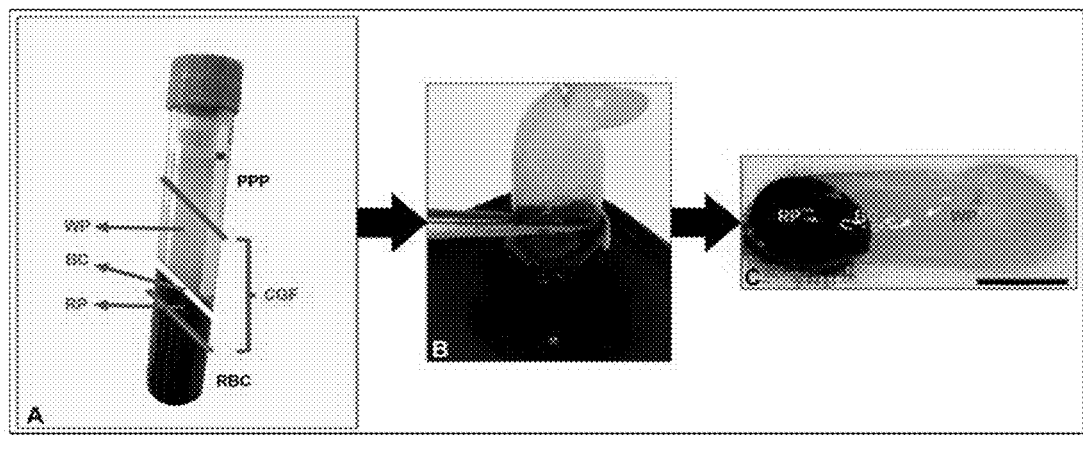

FIG. 4A illustrates a whole blood sample after centrifugation in a test tube in the absence of an anti-coagulating agent.

FIG. 4B shows a clotted CGF layer separated from the rest of the centrifuged whole blood.

FIG. 4C shows a clotted CGF layer laid onto a gauze.

FIG. 5A schematically illustrates and FIG. 6A is a photograph of a device comprising a container covered with a cover to which an artificial bone implant is attached, when the container is filled with whole blood.

FIG. 5B schematically illustrates and FIG. 6B is a photograph of a device comprising a container covered with a cover to which an artificial bone implant is attached, when the container is filled with whole blood after centrifugation.

FIG. 5C schematically illustrates and FIG. 6C is a photograph of an artificial bone implant attached to a cover of the device after the cover and artificial bone implant were separated from the container, after centrifugation with whole blood.

Figure 7:
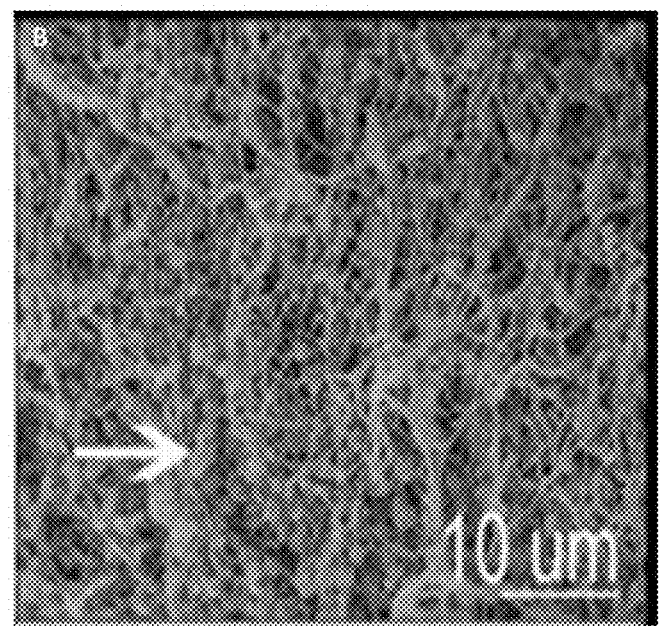

FIG. 7 is a scanning electron micrograph (SEM) of the coating layer covering the artificial bone implant after centrifugation with whole blood seen in FIG. 6C.

Figure 8:

FIG. 8 is a photograph of another embodiment of an artificial bone implant coated with CGF following centrifugation with whole blood.

FIGS. 9A-9E show graphs of cumulative release of growth factors from coated implants over time.

FIGS. 10A-10D are SEM images of CGF-coated dental implants cultured with MSCs. FIG. 10A: A dental implant. FIG. 10B: A CGF-coated dental implant. FIG. 10C: An MSC-seeded dental implant. FIG. 10D: A CGF-coated dental implant incubated with MSCs.

FIGS. 11A-11D are SEM images of treated dental implant surfaces. FIG. 11A: A dental implant surface. FIG. 11B: A CGF-coated dental implant surface. The arrow indicates a platelet. FIG. 11C: An MSC-seeded dental implant surface. The arrow indicates a seeded cell. FIG. 11D: A CGF-coated dental implant incubated with MSCs.

Figure 12:
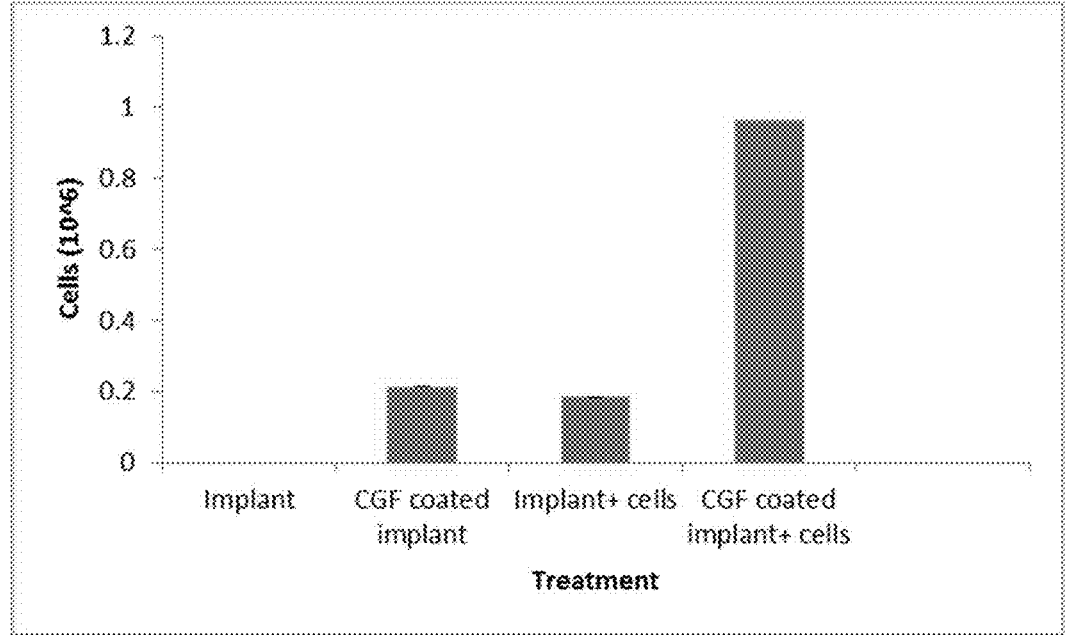

FIG. 12 is a graph showing number of MSCs growing on implant surfaces for two days.

Figure 13A:
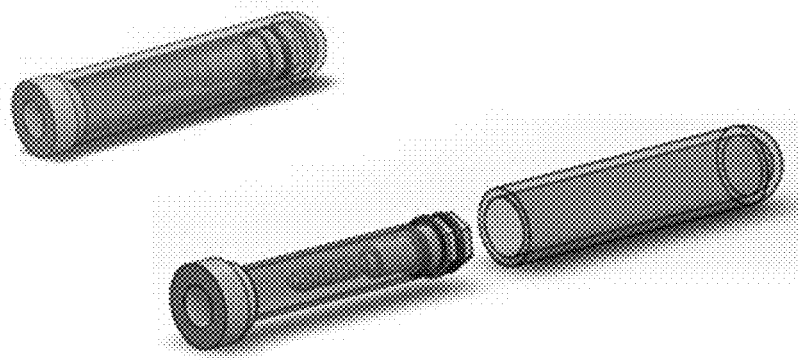
Figure 13B:
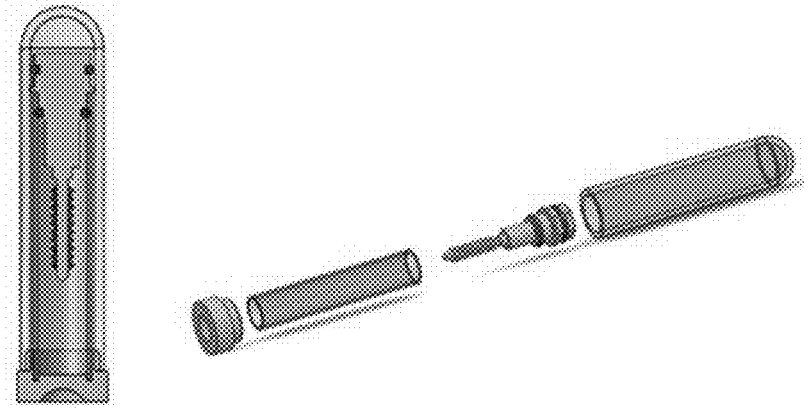
Figure 13C:
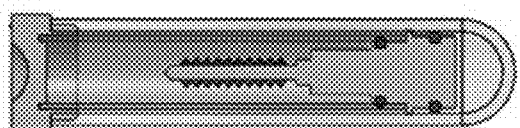

FIGS. 13A-13C schematically illustrate another exemplary embodiment of the device configured to coat a dental implant.

Figure 14A:
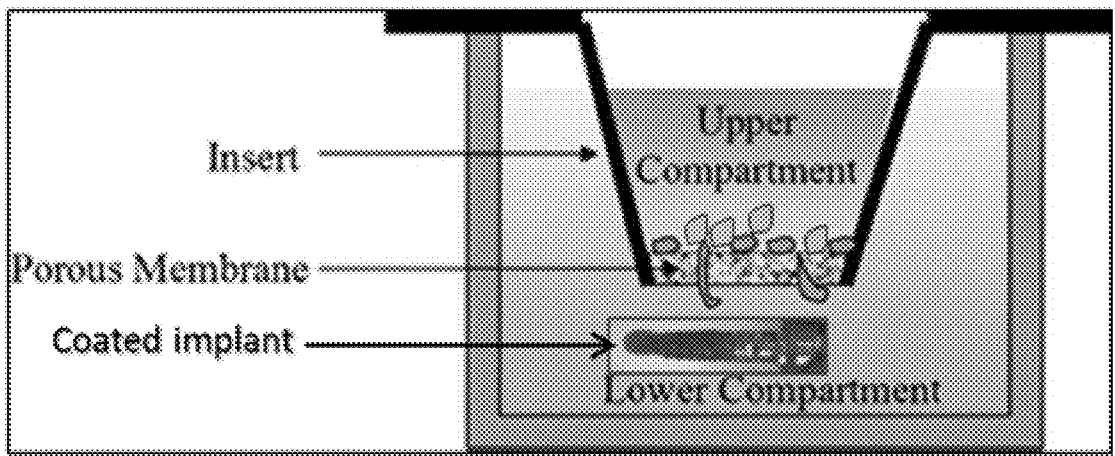
Figure 14B:
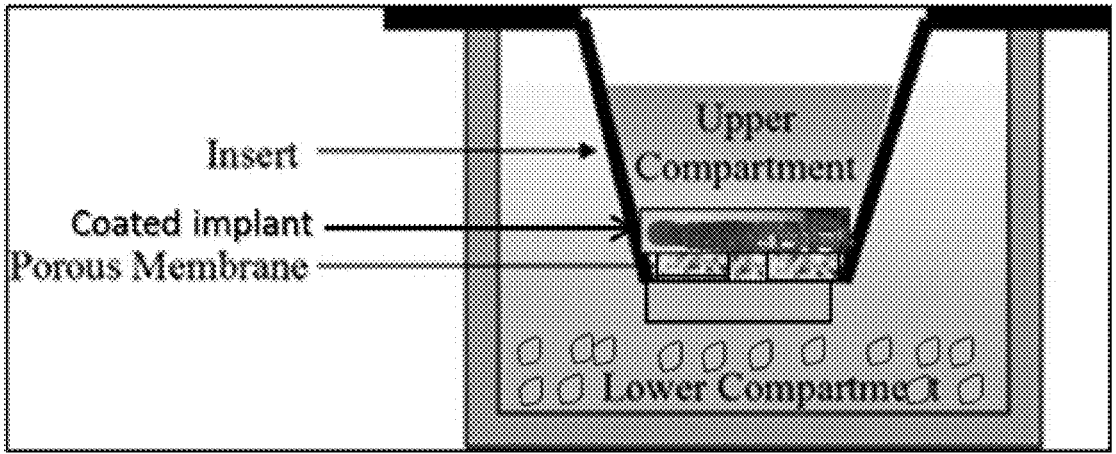

FIGS. 14A and 14B illustrate a Boyden chamber to assess the effect of CGF-coated implants on MSC migration and growth rate.

Figure 15:
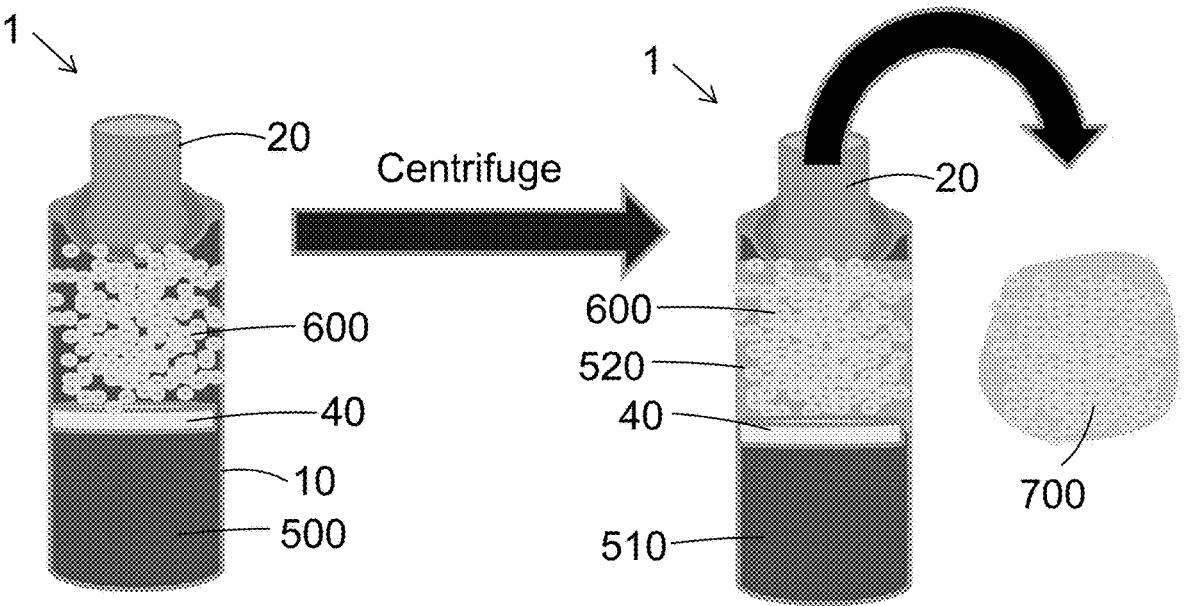

FIG. 15 schematically illustrates, another exemplary embodiment of the device configured to form a putty bone from a bone material, for example bone substitute.

Figure 16:
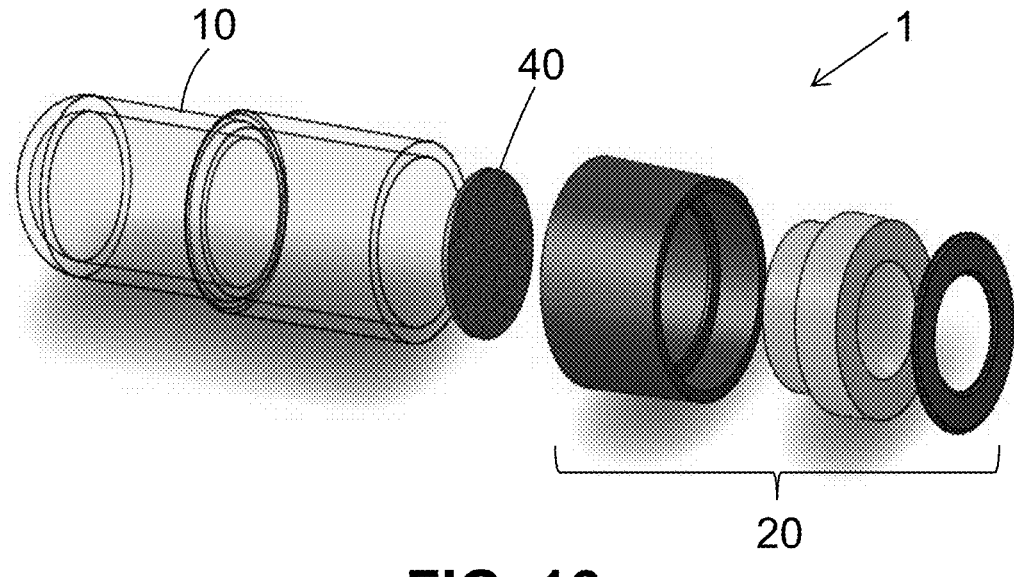

FIG. 16 schematically illustrates, according to an exemplary embodiment, a disassembled device configured to form a putty bone from a bone material.

Figure 17:
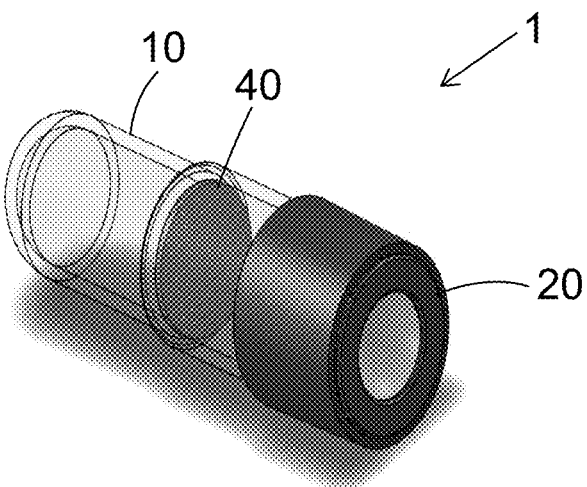

FIG. 17 schematically illustrates, according to an exemplary embodiment, an assembled device configured to form a putty bone from a bone material.

Figure 18:
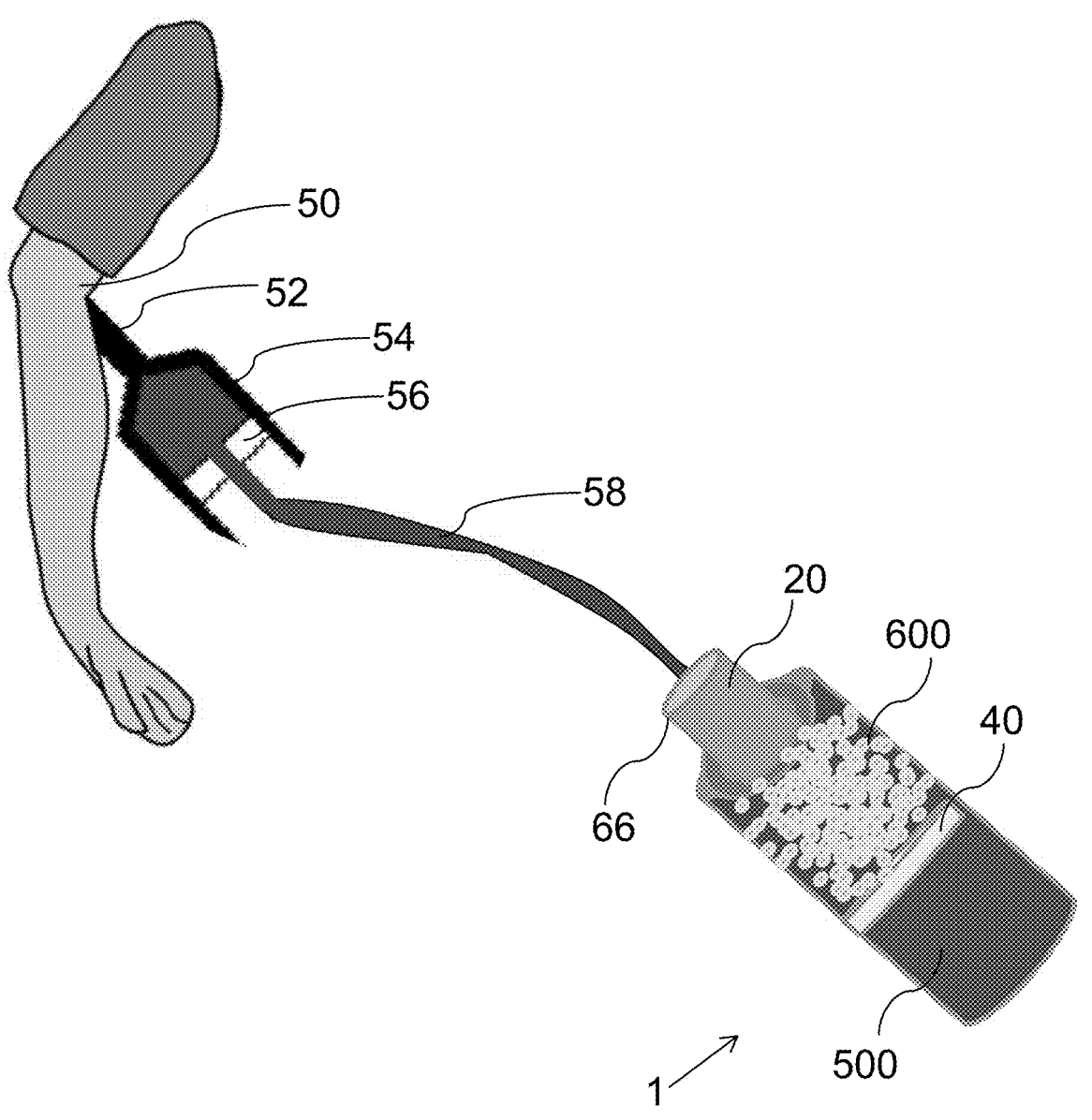
Figure 19A:
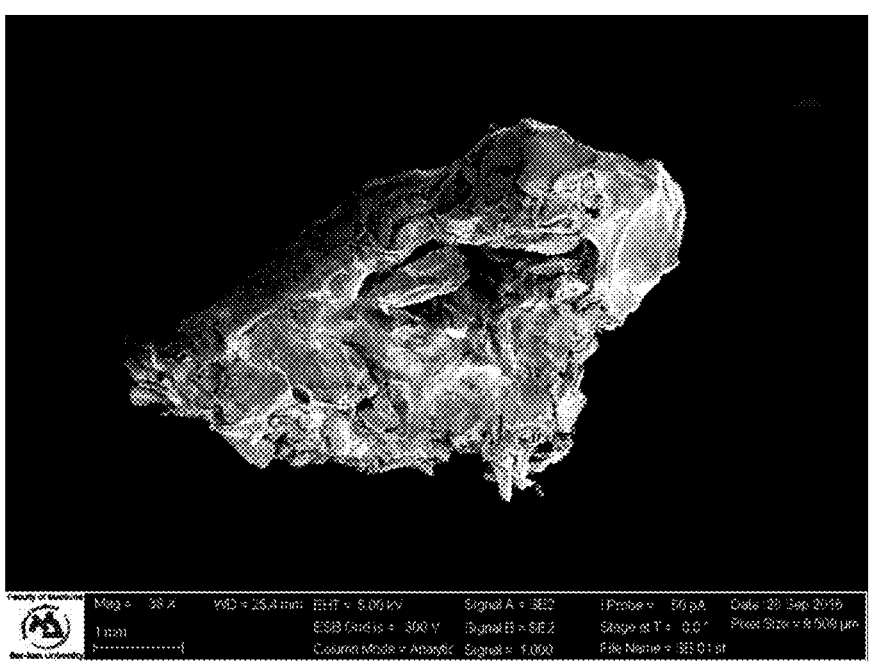
Figure 19B:
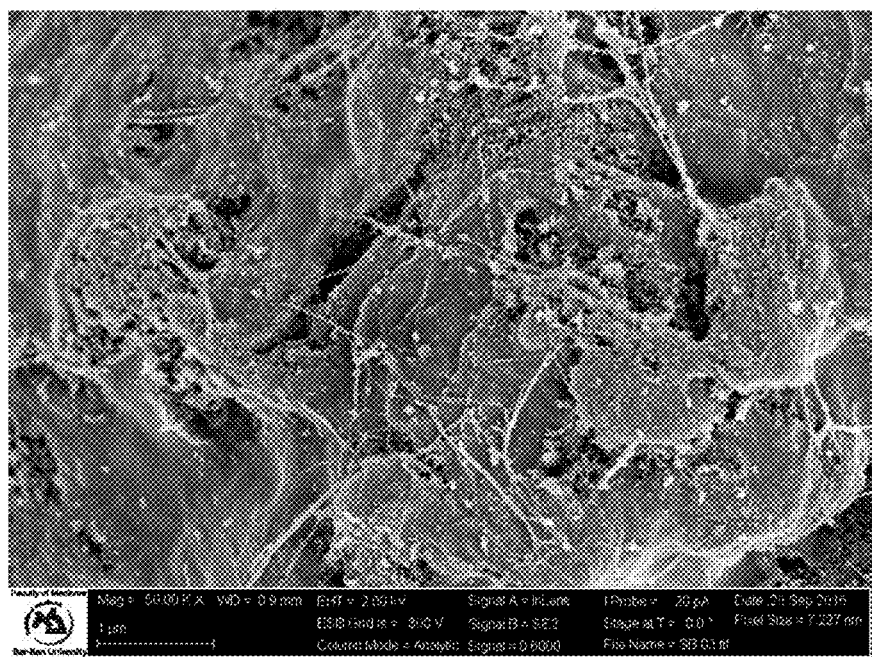
Figure 19C:
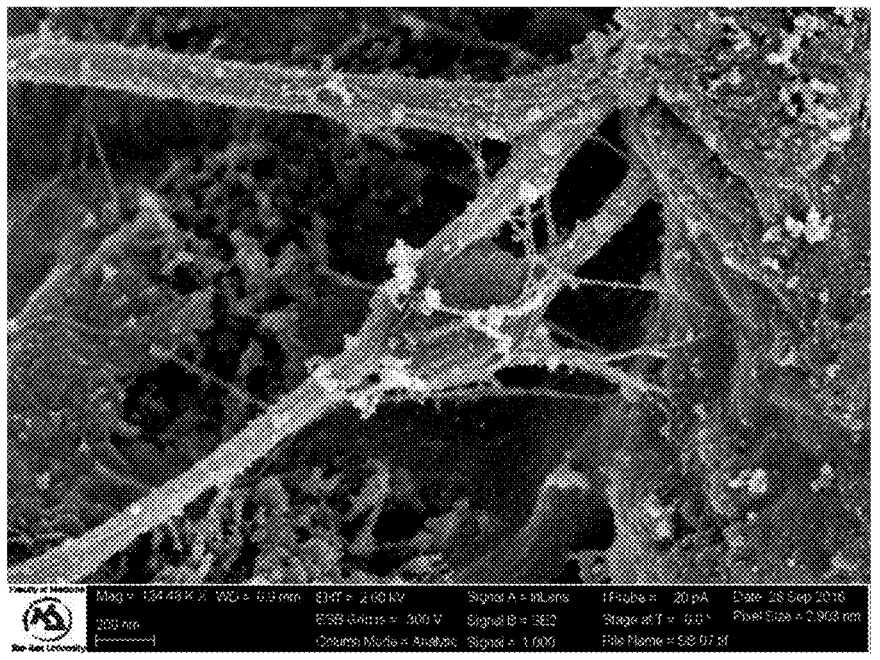
Figure 19D:
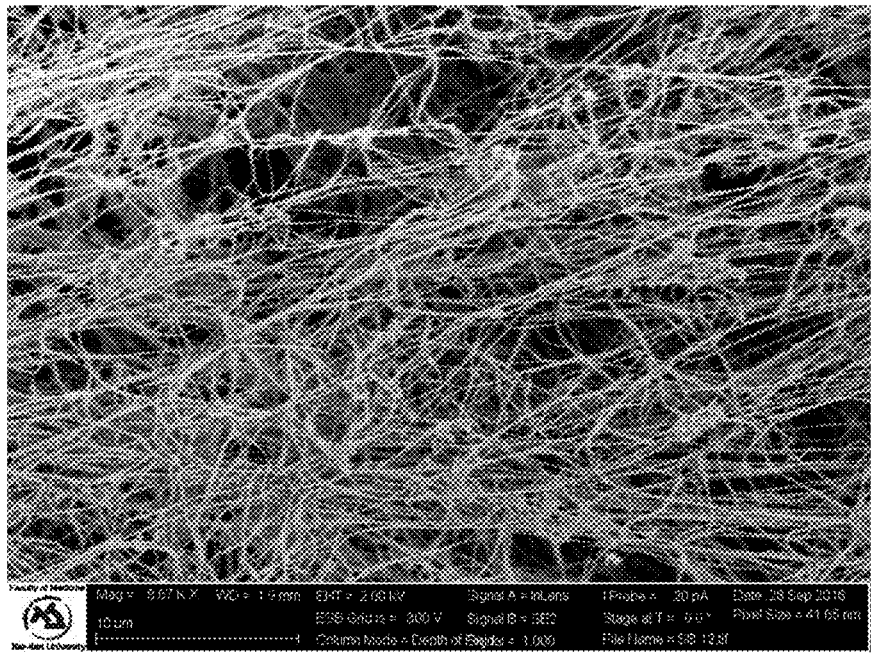
Figure 19E:
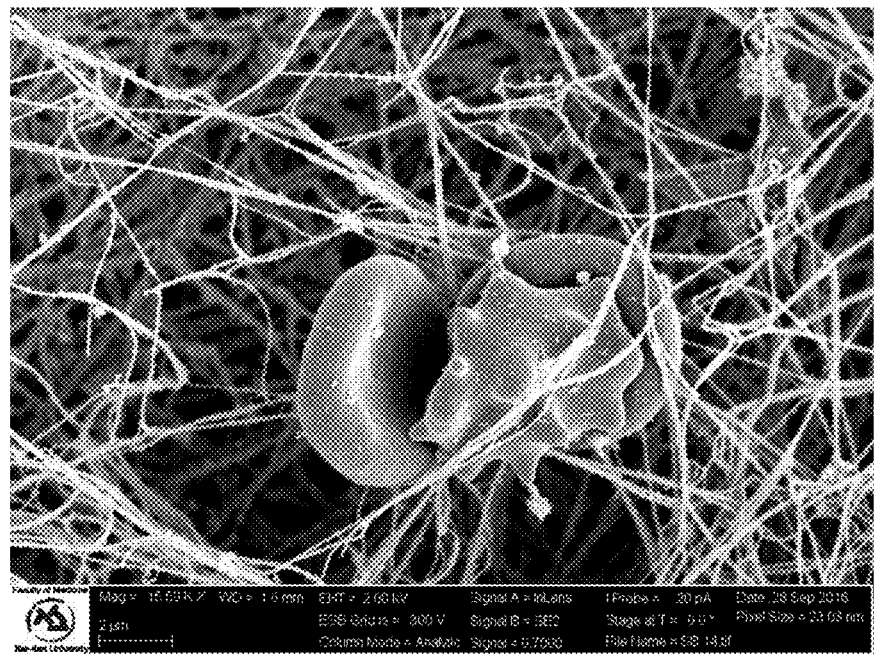
Figure 19F:
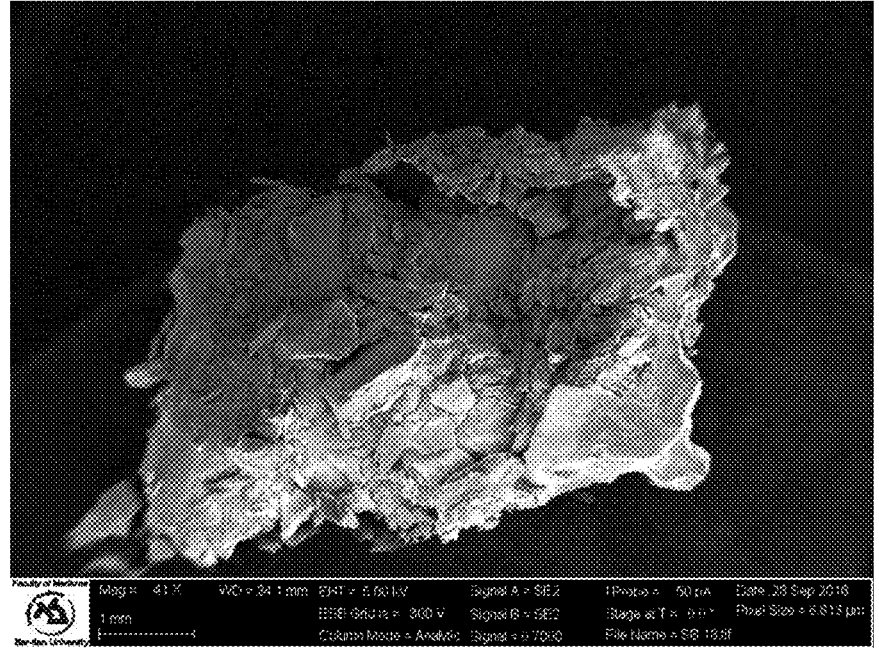
Figure 19G:
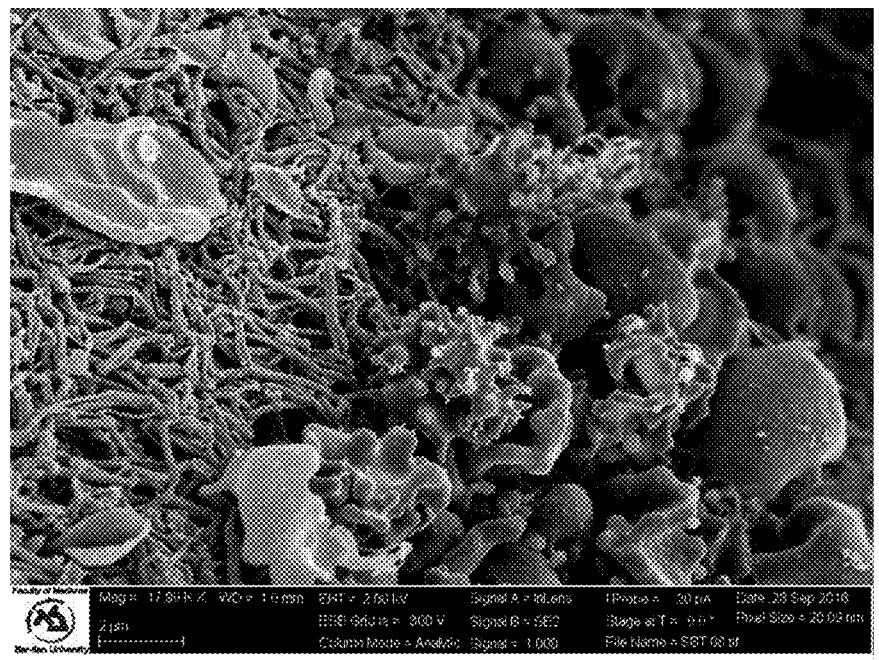
Figure 19H:
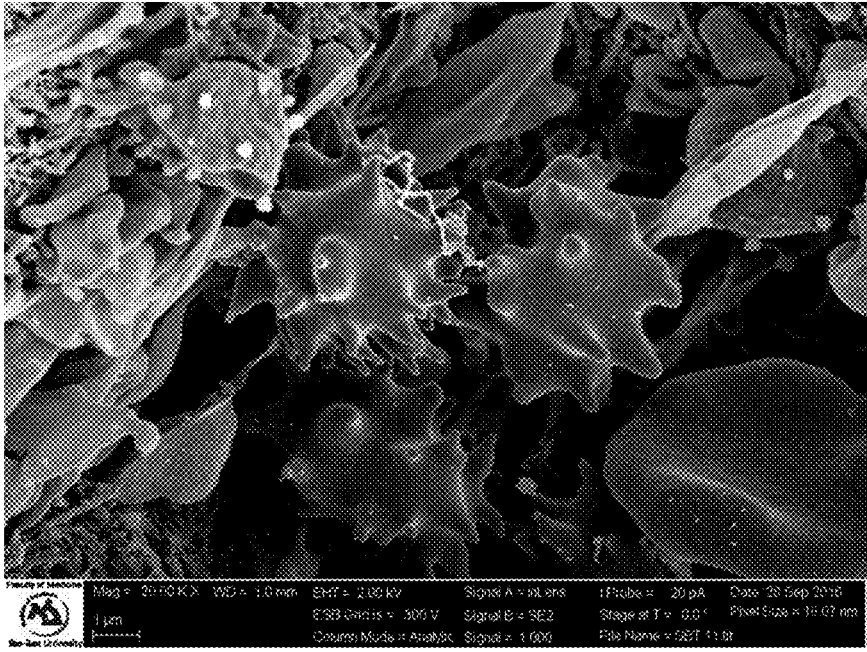
Figure 19I:
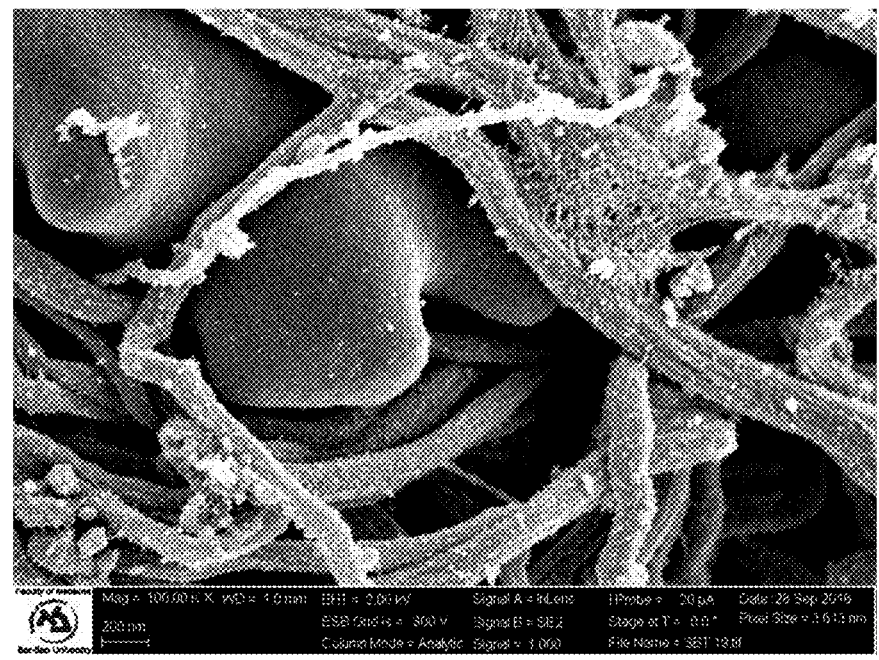

FIG. 18 schematically illustrates, according to an exemplary embodiment, a system for withdrawing whole blood from a vein directly from a vein of a patient into a device configured to form a putty bone from a bone material.

FIGS. 19A-19I are SEM images of a putty bone 700 prepared by using the device 1 configured to form a putty bone from a bone material.

DESCRIPTION OF THE PREFERRED EMBODIMENTS

Before explaining at least one embodiment in detail, it is to be understood that the subject matter is not limited in its application to the details of construction and the arrangement of the components set forth in the following description or illustrated in the drawings. The subject matter is capable of other embodiments or of being practiced or carried out in various ways. Also, it is to be understood that the phraseology and terminology employed herein is for the purpose of description and should not be regarded as limiting. In discussion of the various figures described herein below, like numbers refer to like parts. The drawings are generally not to scale.

For clarity, non-essential elements were omitted from some of the drawings.

The term "artificial bone implant" as disclosed herein refers to any type of artificial bone implant known in the art. Examples of an artificial bone implant include, but not limited to, an artificial bone implant made of a biocompatible material, like titanium, that is used in various procedures—for example an artificial dental implant. Other examples include, but not limited to, bone substitute in any form known in the art—powder, granules, and the like.

One of the currently available methods for accelerating osseointegration of an artificial bone implant is covering the artificial bone implant with whole blood before the placement of the artificial bone implant in the target bone tissue. Whole blood comprises components, designated hereinafter "osseointegration accelerators", that accelerate osseointegration, for example progenitor cells, growth factors that are contained in a blood plasma, and the like.

Preferably, the blood sample used for treating the artificial bone implant is an autologous blood sample, namely a whole blood sample taken from the patient that is subject to the implantation of the artificial bone implant.

It should be noted that the term "patient" as disclosed herein refers to any organism that is subject to artificial bone implantation, namely any animal patient, including a human patient.

The current practice is to immerse the artificial bone implant in a sample of whole blood, preferably an autologous whole blood sample, just before placing the artificial bone implant in a target bone tissue. During the immersion, whole blood including osseointegration accelerators is adhered to the artificial bone implant. Then, the artificial bone implant is separated from the remaining whole blood sample and placed in a target bone tissue. However, it is appreciated that this method is cumbersome, messy, time consuming, and may expose the artificial bone implant covered with the whole blood to non-sterile conditions that may increase the chance of contamination of the artificial bone implant, for example with pathogenic viruses and bacteria that may cause local infection of the tissue surrounding the implantation site, and even systemic life threatening infection.

The present subject matter provides a device for treating an artificial bone implant with whole blood, in a simple, rapid and easy to use way.

The present subject matter yet further provides a device for biologically activating a surface of an artificial bone implant with whole blood, in a simple, rapid and easy to use way.

The present subject matter still further provides a device for biologically activating a surface of an artificial bone implant with whole blood, in order to accelerate osseointegration of the artificial bone implant, in a simple, rapid and easy to use way.

More particularly, the present subject matter provides a device for biologically activating a surface of an artificial bone implant with whole blood, in order to enhance osteoblastic migration, adhesion, proliferation, and differentiation, all key to improved osseointegration as well as shorten the period of the implant site rehabilitation.

The present subject matter additionally provides methods for treating an artificial bone implant with whole blood, using the subject matter's device.

The present subject matter yet additionally provides methods for biologically activating a surface of an artificial bone implant with whole blood, using the subject matter's device.

The present subject matter still additionally provides methods for biologically activating a surface of an artificial bone implant with whole blood, in order to accelerate osseointegration of the artificial bone implant, using the subject matter's device.

More particularly, the present subject matter provides methods for biologically activating a surface of an artificial bone implant with whole blood, in order to enhance osteoblastic migration, adhesion, proliferation, and differentiation, all key to improved osseointegration as well as shorten the period of the implant site rehabilitation.

It should be noted that for the sake of simplicity only, whole blood will be occasionally designated hereinafter shortly as "blood".

Figure 1:
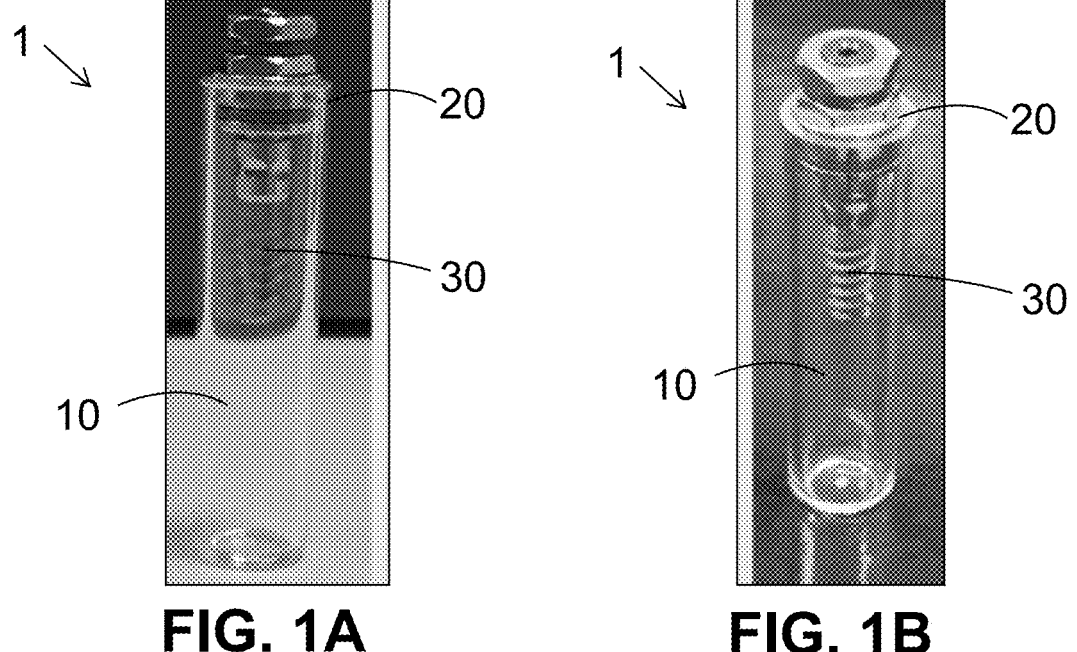
FIGS. 1A and 1B illustrate, according to an exemplary embodiment, a side view and a perspective view, respectively, of a device for treating an artificial bone implant with whole blood.

FIGS. 1A and 1B illustrate, according to an exemplary embodiment, a side view and a perspective view, respectively, of a device 1 for treating an artificial bone implant with whole blood. According to a preferred embodiment, the device 1 is configured to allow coverage of an artificial bone implant with osseointegration accelerators that are present in the whole blood. According to one embodiment, the device 1 comprises a container 10 having an opening 15 (not seen), and a cover 20 configured to cover the opening 15 of the container 10. The container 10 is configured to accommodate any artificial bone implant 30 known in the art, in any size and structure. According to a preferred embodiment, the artificial bone implant 30 is made of a biocompatible material, for example titanium. For the sake of simplicity only, the artificial bone implant 30 is occasionally designated hereinafter "implant 30." FIGS. 1A and 1B further illustrate an exemplary implant 30 in the form of a dental implant 30 that is accommodated in the container 10. According to a preferred embodiment, the cover 20 is configured to attach to the implant 30 so that the implant 30 is held by the cover 20. According to one embodiment, the height of the container 10 is similar to the length of the implant 30. According to another embodiment, the height of the container 10 is higher than the length of implant 30, as illustrated in FIGS. 1A and 1B. According to yet another embodiment, the container 10 is configured to be filled with whole blood in a manner that allows immersion of an implant 30 in the whole blood when the implant 30 is attached to the cover 20 and the cover 20 covers the container 10.

According to one embodiment, whole blood is transferred into the container 10 through the opening 15, for example with a syringe or a pipette. However, this way of transferring whole blood into the container 10 is tedious, time consuming, and more importantly increases the chance of exposure of the whole blood sample and the artificial bone implant 30 to non-sterile conditions. In order to overcome this problem, according to another embodiment, whole blood is transferred into the container 10 while keeping the container 10 sealed by the cover 20. This may be achieved, for example, by maintaining a negative air pressure inside the container 10, and transferring whole blood into the container 10 using a device that that penetrates into the interior of the container 10, for example through the cover 20, or through a bottom 17 of the container (see FIGS. 1A and 1B), or through any part of the container 10.

It should be noted that the term "negative air pressure" will occasionally be referred to hereinafter shortly as "vacuum". Accordingly, a component, for example a container 10, having a negative air pressure will occasionally be referred to hereinafter shortly as "vacuumed" component, for example "vacuumed container".

Therefore, according to a further embodiment, the container 10 and the cover 20 are configured to maintain a negative air pressure in the container 10 compared to an ambient air pressure. According to a yet further embodiment, the cover 20 is configured to allow penetration of a needle-like device into an interior of the container 10. According to still a further embodiment, the negative air pressure in the container 10 is in a level that allows entrance of a quantity of whole blood into the container 10 that is enough to cover an artificial bone implant 30 held by the cover 20. These embodiments allow transfer of whole blood into the container 10 to cover an artificial bone implant 30 held inside the container 10 by the cover 20, without a need to open the cover 20, thus avoiding exposure of the whole blood and the artificial bone implant 30 to non-sterile conditions.

According to one embodiment, the whole blood is transferred into the sealed container 10 having a negative air pressure within, from a whole blood source. Examples of a whole blood source include a syringe containing whole blood, a blood bag, a vein of a patient, and the like. A preferred embodiment of the whole blood source is a vein of a patient. According to another preferred embodiment, the whole blood is transferred from a vein of a patient that is subject to the implantation of the artificial bone implant 30, namely the whole blood sample that is used to treat the artificial bone implant 30 is an autologous blood sample.

According to one embodiment, there is provided a method for covering an artificial bone implant 30 with osseointegration accelerators before implanting the artificial bone implant 30 in a target bone tissue, the method comprising:

providing a device 1 for treating an artificial bone implant with whole blood, the device comprising a container 10 having an opening 15, and a cover 20 configured to cover the opening 15 and hold an artificial bone implant 30;

attaching an artificial bone implant 30 to the cover 20;

providing a whole blood sample;

filling the container 10 with the whole blood sample;

covering the container 10 with the cover 20 holding the artificial bone implant 30 in a manner that at least part of the artificial bone implant 30 is immersed in the whole blood;

incubating the artificial bone implant 30 in the whole blood for a period of time that allows covering of the artificial bone implant 30 with osseointegration accelerators;

removing the cover 20 with the osseointegration accelerators-covered artificial bone implant 30 from the container 10; and detaching the osseointegration accelerators-covered artificial bone implant from the cover.

When a device 1 in which there is a negative air pressure in the container 10 is used for covering an artificial bone implant 30 with osseointegration accelerators before implanting the artificial bone implant 30 in a target bone tissue, the following embodiments apply.

According to one embodiment, there is provided a method for storing an artificial bone implant 30 in a device 1 for treating an artificial bone implant with whole blood under negative air pressure conditions, the method comprising:

providing a device 1 for treating an artificial bone implant with whole blood, the device comprising a container 10 having an opening 15, and a cover 20 configured to seal the opening 15, wherein the container 10 and the cover 20 are configured to maintain a negative air pressure in the container 10, the cover 20 is configured to allow penetration of a needle-like device into an interior of the container 10, and the cover 20 is further configured to hold an artificial bone implant 30;

attaching an artificial bone implant 30 to the cover 20;

sealing the opening 15 of the container 10 with the cover 20 to which an artificial bone implant 30 is attached, in a manner that the artificial bone implant 30 is contained in the container 10; and creating a negative air pressure in the container 10.

The creation of a negative air pressure in the container 10 is by any method known in the art, for example, withdrawing air from the container 10 using a needle-like device that penetrates the cover 20, while maintaining the container 10 sealed by the cover 20.

The method for storing an artificial bone implant 30 in a device 1 under negative air pressure conditions may be performed, for example, during the manufacturing of devices 1 for treating an artificial bone implant with whole blood that contain the artificial bone implant 30 under negative air pressure conditions. Such devices 1 are ready-to-use, thus rendering the process of treating the artificial bone implant 30 with whole blood a rapid and easy to use procedure, preventing exposure of the artificial bone implant 30 and the whole blood to non-sterile conditions.

Usage of a device 1 prepared by the aforementioned method may be according to the following exemplary embodiments.

According to one embodiment, there is provided a method for covering an artificial bone implant 30 with osseointegration accelerators before implanting the artificial bone implant 30 in a target bone tissue, the method comprising:

providing a device 1 for treating an artificial bone implant with whole blood, comprising a container 10 sealed with a cover 20, and containing an artificial bone implant 30 attached to the cover 20 under negative air pressure conditions;

inserting into an interior of the container 10 a needle-like device fluidically connected to a whole blood source;

letting the whole blood filling the interior of the container 10 and covering at least part of the artificial bone implant;

incubating the artificial bone implant 30 in the whole blood for a period of time that allows covering of the artificial bone implant 30 with osseointegration accelerators;

removing the cover 20 with the osseointegration accelerators-covered artificial bone implant 30 from the container 10; and detaching the osseointegration accelerators-covered artificial bone implant from the cover.

According to one embodiment, the whole blood source contains autologous whole blood sample.

According to another embodiment, the whole blood source is a syringe containing whole blood.

According to yet another embodiment, the whole blood source is a blood bag containing whole blood.

According to a preferred embodiment, the whole blood source is a vein of a patient.

When the whole blood source is a vein of a patient, preferably a vein of a patient that is subject to the implantation of the artificial bone implant 30, a needle-like device that is inserted in to the patient's vein is fluidically connected with a conduit to the needle-like device that is inserted into the interior of the container 10 through the cover 20. As a result of the negative air pressure inside the container 10, whole blood is withdrawn from the patient's vein, through the conduit, into the container 10.

Figure 2:
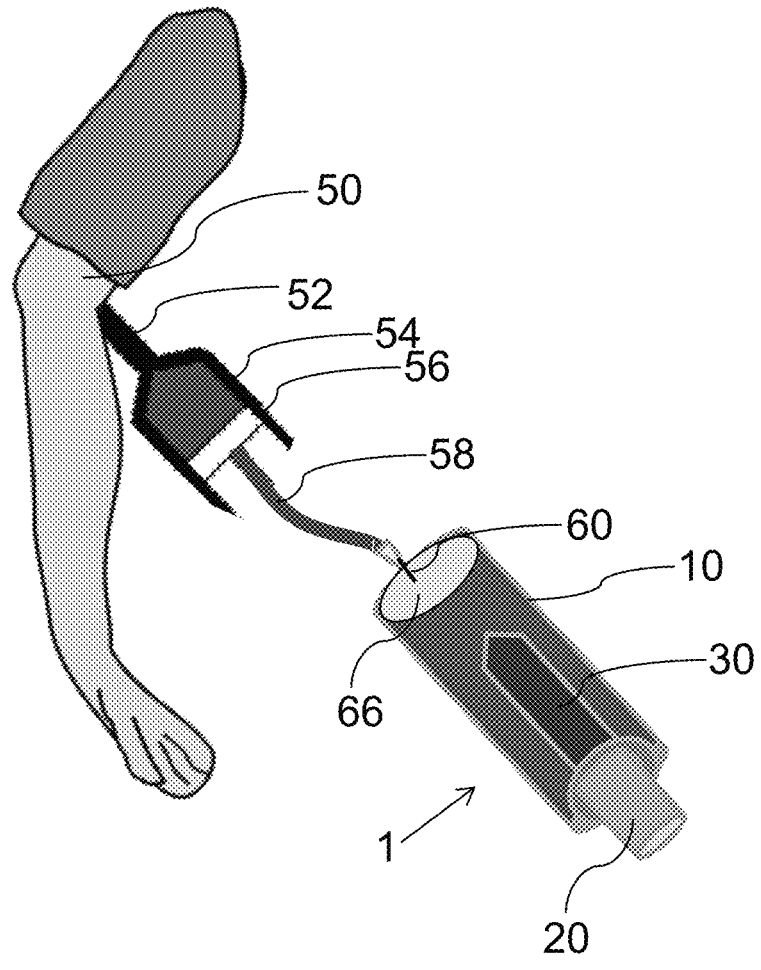
FIG. 2. schematically illustrates, according to an exemplary embodiment, a system for withdrawing whole blood from a vein directly from a vein of a patient into a device containing an artificial bone implant.

FIG. 2. schematically illustrates, according to an exemplary embodiment, a system for withdrawing whole blood from a vein directly from a vein of a patient into a device 1 containing an artificial bone implant 30. According to a preferred embodiment, whole blood is withdrawn from a vein of a patient, for example a vein in a patient's hand 50, by venipuncture as known in the art, using for example a hypodermic needle 52, configured to be inserted into a vein, fluidically attached to a sheath 54, configured to receive whole blood. The sheath is provided with a plug 56, configured to plug the sheath and allow insertion of a tube 58 into the interior of the sheath 54. The tube 58 comprises a first end, configured to be inserted into the sheath 54 through the plug 56, and a second end configured to penetrate into the container 10 of the device. This is achieved, for example, by a second needle 60 attached to the second end of the tube 58. The second needle 60 is configured to penetrate into the container 10 of the device 1, and the device 1 is configured to allow penetration of a second needle 60 through it. This is achieved, for example, by using a container comprising, for example, a rubber membrane 66 at its base, namely at the side of the container 10 opposite to the cover 20 to which the artificial bone implant 30 is attached. The rubber membrane 66 is configured to allow penetration of a second needle 60 into the interior of the container 10. Thus, upon insertion of the hypodermic needle 52 into a patient's vein, penetration of the first end of the tube 58 into the sheath 54 fluidically connected to the hypodermic needle 52, and penetration of the second needle 60, that is attached to the second end of the tube 58, into the container 10 interior, there is provided a direct route through which whole blood is withdrawn from a patient's vein directly into the container 10 containing the artificial bone implant 30. The negative air pressure in the container assists in withdrawing blood from the patient's vein directly into the container 10.

One advantage of this embodiment is that it eliminates exposure of the whole blood and of the artificial bone implant to non-sterile conditions in one hand, and allows coverage of the artificial bone implant with whole blood in a simple, rapid and easy way.

During experimentation of the aforementioned method for covering an artificial bone implant 30 with osseointegration accelerators before implanting the artificial bone implant 30 in a target bone tissue, it was surprisingly found that using a whole blood sample devoid of an anti-coagulating agent is beneficial over the usage of a whole blood sample comprising anti-coagulating agents, for example heparin, citrate, and the like. It was found that clotting of blood over the artificial bone implant 30 causes more efficient coverage of the artificial bone implant 30 with osseointegration accelerators.

Thus, according to another preferred embodiment, relating to the method for covering an artificial bone implant 30 with osseointegration accelerators before implanting the artificial bone implant 30 in a target bone tissue, the whole blood sample is devoid of anti-coagulating agents.

During experimentation it was further found that centrifugation of device 1 for treating an artificial bone implant 30 with whole blood, while in the container there is an artificial bone implant 30 covered with whole blood devoid of an anti-coagulating agent, causes a very efficient coverage of the artificial bone implant 30 with osseointegration accelerators.

Thus, according to an additional embodiment, the device 1 for treating an artificial bone implant with whole blood is configured to be centrifuged while containing an artificial bone implant covered with whole blood.

According to yet an additional embodiment, relating to the method for covering an artificial bone implant 30 with osseointegration accelerators before implanting the artificial bone implant 30 in a target bone tissue, the incubating is centrifuging the device 1 for a period of time that allows covering of the artificial bone implant 30 with osseointegration accelerators comprises.

According to still an additional embodiment, the centrifuging is at a range of substantially 2,500-3,500 g and at a time range of substantially 7-10 min.

Figure 3:
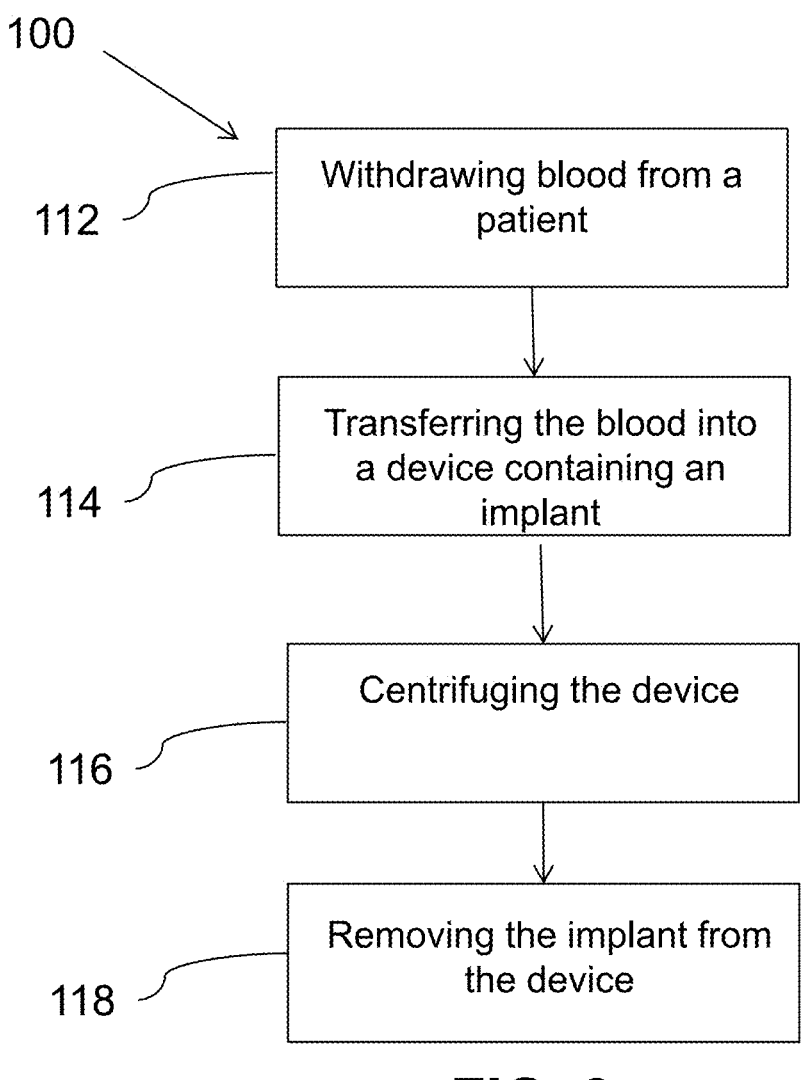
FIG. 3 schematically illustrates, according to an exemplary embodiment, a preferred embodiment of the method for covering an artificial bone implant with osseointegration

FIG. 3 schematically illustrates, according to an exemplary embodiment, a preferred embodiment of the method for covering an artificial bone implant 30 with osseointegration accelerators before implanting the artificial bone implant 30 in a target bone tissue, using the device 1 of the present subject matter, the method 100 comprises:

withdrawing blood from a patient (112)—preferably the blood is withdrawn from a vein of a patient in the body of which the artificial bone implant 30 is to be implanted;

transferring the blood into a device 1 containing an implant (114)—preferably the device comprises a vacuumed container containing an implant, and the blood is transferred into the vacuumed container in order to cover the implant;

centrifuging the device 1 (116)—according to a preferred embodiment, the container is centrifuged at a range of substantially 2,500-3,000 g for substantially 7-10 minutes; and removing the implant from the device.

FIG. 4A illustrates a whole blood sample after centrifugation in a test tube in the absence of an anti-coagulating agent. During centrifugation, whole blood is separated to three major layers: an upper plasma layer, also known as platelet poor plasma (PPP), a lower red blood cells (RBC) layer, and a solid middle layer, designated hereinafter concentrated growth factors (CGF) layer. The solid CGF layer comprises three parts: an upper white part (WP), comprising white blood cells (WBC) and platelets, a lower red part (RP), and a middle "buffy coat" (BC) part. Since the whole blood was centrifuged in the absence of an anti-coagulating agent, the CGF layer is clotted.

FIG. 4B shows a clotted CGF layer separated from the rest of the centrifuged whole blood.

FIG. 4C shows a clotted CGF layer laid onto a gauze.

The biomaterial for coating dental implants is mainly composed of autologous concentrated growth factors (CGF). It is prepared of whole venous blood collected in sterile tubes without an anticoagulant. After centrifugation, a dense fibrin clot/block rich in growth factors, is produced. Fibrin clot/block is produced as a result of high concentration of fibrinogen, factor XIII and thrombin. Factor XIII, which is activated by thrombin, crosslinks fibrinogen to fibrin clot, increases stability and strength as well as protects against plasmin-mediated degradation. Essentially, the strengthened fibrin matrix captures multiple growth factors such as platelet-derived growth factor, transforming growth factor-ß, vascular endothelial growth factor and epidermal growth factor.

FIG. 5A schematically illustrates and FIG. 6A is a photograph of a device 1 comprising a container 10 covered with a cover 20 to which an artificial bone implant 30 is attached, when the container 10 is filled with whole blood 500.

FIG. 5B schematically illustrates and FIG. 6B is a photograph of a device 1 comprising a container 10 covered with a cover 20 to which an artificial bone implant 30 is attached, when the container 10 is filled with whole blood after centrifugation, for example at a range of substantially 2,500-3,000 g for substantially 7-10 minutes. As a result of the centrifugation the whole blood 500 is separated to two main layer—a lower layer 510 comprising red blood cells and platelets, and an upper layer 520 comprising plasma.

FIG. 5C schematically illustrates and FIG. 6C is a photograph of an artificial bone implant 30 attached to a cover 20 of the device 1 after the cover 20 and artificial bone implant 30 were separated from the container 10, after centrifugation with whole blood 500. The artificial bone implant 30 is covered with some of the upper layer 520 comprising plasma.

The artificial bone implant 30 is held by the cover 20 inside the container 10 in a manner that after centrifugation the artificial bone implant 30 is in contact with the upper plasma layer, the middle buffy coat layer, and some upper part of the lower red blood cells layer. Thus, the centrifugation separates the artificial bone implant from most of the red blood cells, but allows direct contact of the artificial bone implant mostly with the plasma, and the white blood cells and platelets of the whole blood sample.

As a result of the centrifugation, plasma and buffy coat is adhered to the surface of the artificial bone implant. Thus, components of plasma and buffy coat adhere to the surface of the artificial bone implant, including osseointegration accelerators such as growth factors that are contained in the plasma layer, and progenitor cells that are contained in the buffy coat layer.

FIG. 7 is a scanning electron micrograph (SEM) of the coating layer covering the artificial bone implant after centrifugation with whole blood seen in FIG. 6C. The coating layer comprises a fibrin network (without interlocked RBCs due to centrifugation). The coating layer on the artificial bone implant is well-woven and characterized by a dense fibrin texture with thin fibers with pores of about 0.1 micrometer.

FIG. 8 is a photograph of another embodiment of an artificial bone implant coated with CGF following centrifugation with whole blood. The fibrin clot coating the artificial bone implant is readily seen.

To clinically justify the use of CGF-coated implants, the biological activity of the coating layer was evaluated using enzyme-linked immunosorbent assay (ELISA). The cumulative release rate of growth factors from the CGF coating layer was studied in vitro, by incubating coated implants in medium, and quantitating the growth factors released into the medium. We chose to study certain growth factors that have a biological effect on cell adhesion, proliferation and osteogenic differentiation, all central to implant osseointegration. These growth factors are mainly released from platelets that are interlocked within the fibrin network. Fibrin clot formation is initiated during centrifugation, where the heavy RBCs sediment first and are therefore not interlocked within the fibrin network, while the lighter WBCs and platelets sediment later, concomitant to fibrin clot formation, and therefore become interlocked in the network. These platelet-rich concentrates within the fibrin clot differentially release growth factors and affect cell differentiation and functions. These growth factors include: platelet derived growth factor (PDGF), which enhance cell growth, blood vessel repair and generation and collagen production; vascular endothelial growth factor (VEGF), which promotes growth and new generation of vascular cells; tumor necrosis factor-alpha (TNF-$\alpha$), which is involved in systemic inflammation; transforming growth factor-beta1 (TGF-ß1), which improves growth and neogenesis of epithelial cells; vascular cells and wound healing; and insulin-like growth factor-1 (IGF-1), which is crucial in healing and cell growth. The kinetics of cumulative release of growth factors from coated implants is presented in FIG. 9.

Figure 9C:
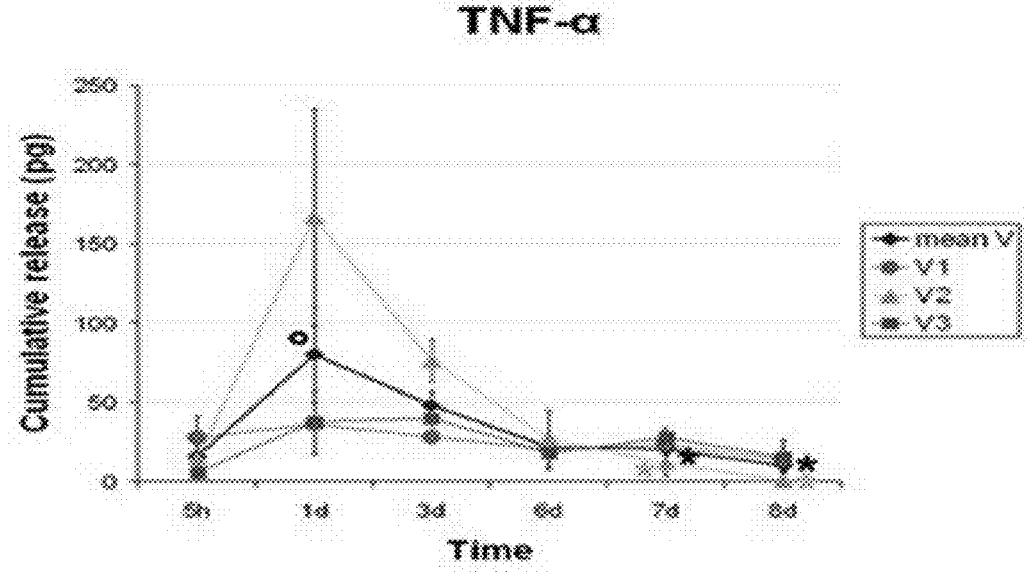
Figure 9D:
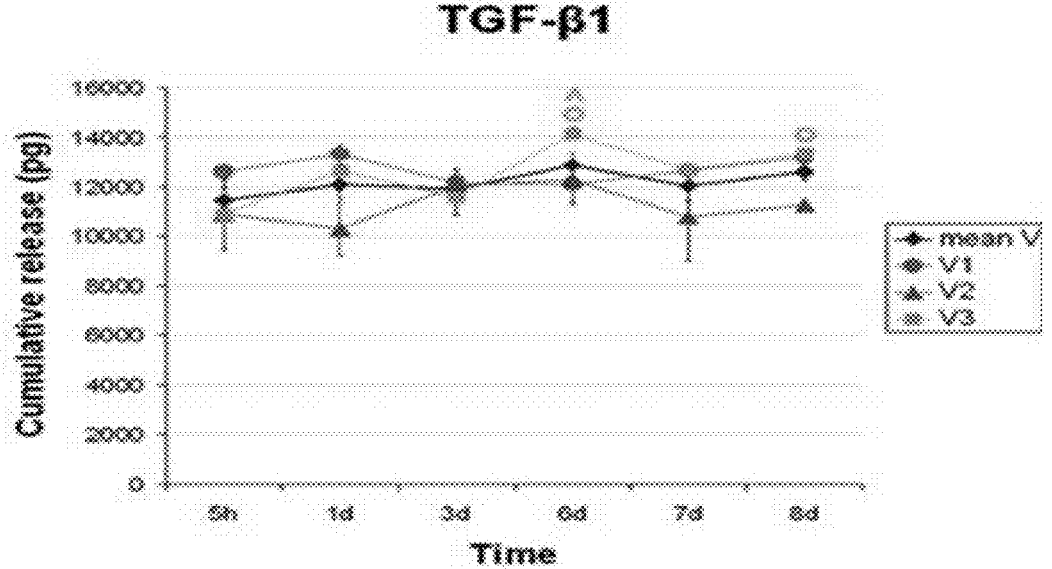
Figure 9E:
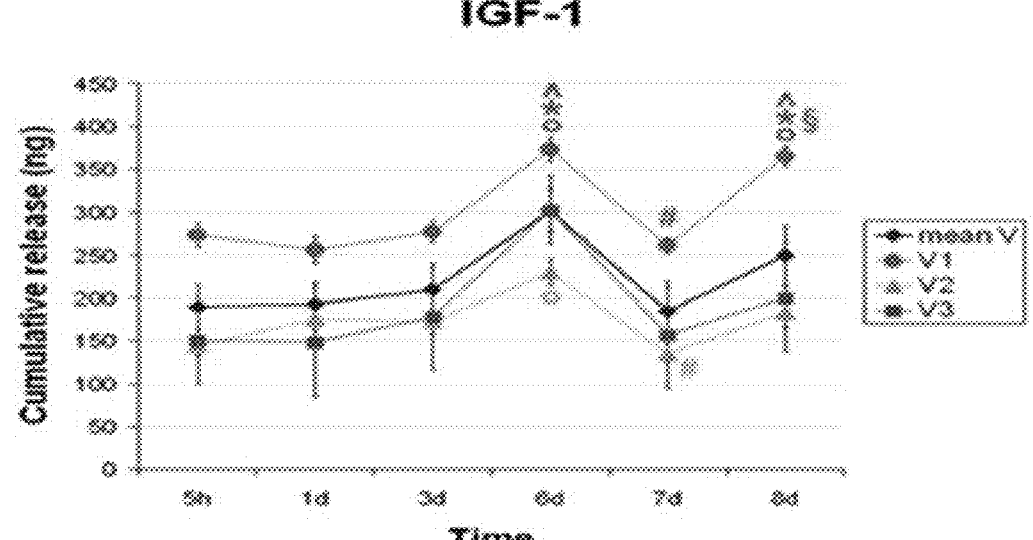

FIGS. 9A-9E show graphs of cumulative release of growth factors from coated implants over time. Coated implants were incubated in medium at 37° C., for varying time intervals (5 h or 1, 3, 6, 7, or 8 days) and growth factors released into the medium were quantitated. The release test was conducted using blood from three different donors, each incubated with an implant in a separate vacuum container (v1, v2, and v3). The individual and mean results are presented. FIG. 9A: PDGF-AB release over time. FIG. 9B: VEGF release over time. FIG. 9C: TNF-$\alpha$ release over time. FIG. 9D: TGF-ß1 release over time. FIG. 9E: IGF-1 release over time.

All tested growth factors were present in the CGF coating layer and released at a slow rate. PDGF-AB and VEGF release seemed to increase over the eight-day period, whereas TNF-$\alpha$, TGF-ß1, and IGF-1 release seemed to be constant over time. Future studies will measure the release of growth factors in media that contain protease inhibitors, to account also for degraded growth factor release. The release of growth factors will be assessed for a longer time; up to 20 days.

SEM was employed to characterize the surface of CGF-coated dental implants seeded with cells. Mesenchymal stem cells (MSCs) isolated from bone marrow were seeded onto CGF-coated implants, at a density of 100,000 MSCs/ml/dental implant, and then cultured for two days. This was performed to verify the effect of CGF coat on cell adhesion and growth. The samples were then fixed in and the three-dimensional morphology of the implant coating and distribution of cells were visualized (FIGS. 10A-10D and 11A-11D).

FIGS. 10A-10D are SEM images of CGF-coated dental implants cultured with MSCs. FIG. 10A: A dental implant. FIG. 10B: A CGF-coated dental implant. FIG. 10C: An MSC-seeded dental implant. FIG. 10D: A CGF-coated dental implant incubated with MSCs.

FIGS. 11A-11D are SEM images of treated dental implant surfaces. FIG. 11A: A dental implant surface. FIG. 11B: A CGF-coated dental implant surface. The arrow indicates a platelet. FIG. 11C: An MSC-seeded dental implant surface. The arrow indicates a seeded cell. FIG. 11D: A CGF-coated dental implant incubated with MSCs. The arrows indicate seeded cells.

The bare titanium dental implant surface (FIG. 11A) differed from CGF-coated implant surface, with the latter displaying fibrin fibers (FIG. 11B). Cells attached to the bare implant surface (FIG. 11C), but were observed in greater numbers on CGF-coated surfaces (FIG. 11D).

After demonstrating the three-dimensional structure of the CGF coating layer and the growth factors release rate, we investigated the biological activity of the CGF coating on bone marrow-derived MSCs. As the CGF coating contains fibrin matrix and growth factors, the adhesion and prolif- eration of MSCs on the layer was tested by the AlamarBlue metabolic activity assay. MSCs were seeded at a density of 100,000 MSCs/ml/dental implant, and the number of cells which adhered to implant surfaces and proliferated for two days was evaluated (FIG. 12).

FIG. 12 is a graph showing number of MSCs growing on implant surfaces for two days. The CGF coating signifi- cantly enhanced MSCs adhesion and proliferation as com- pared to the control samples. The biocompatibility of the fibrin matrix and the effect of the interlocked factors on cell growth are projected to enhance MSC osteogenic differen- tiation. We investigate the effect of the CGF coating on osteogenic genes, using techniques such as fluorescence- activated cell scanner (FACS) and real-time PCR.

FIGS. 13A-13C schematically illustrate another exem- plary embodiment of the device 1 configured to coat a dental implant. FIG. 13A illustrates a vacuum container comprising two tubes. Blood is transferred into the inner tube, in which a dental implant is placed. The larger tube protects the inner tube during centrifugation. FIG. 13B illustrates an assembled vacuum container centrifuged with a silicon cap facing down. FIG. 13C illustrates a silicon cap from which blood is transferred.

FIGS. 13A-13C illustrate the vacuum container in which a dental implant is positioned such that root surface coating occurs upon centrifugation. The appropriate pressure of vacuum within the vacuum container is set up to withdraw the precise amount of blood for optimal coating. Accelera- tion of blood clotting may be achieved by coating the inner lumen of the vacuum container with silicone and micronized silica. As such, the blood withdrawn into the vacuum container undergoes a complex clotting cascade forming long strands of fibrin around the implant that eventually results in a homogeneous net-like texture. Taken together, the parameters of vacuum and centrifugation (e.g., relative centrifugal force (rcf), time, speed, orientation of container in centrifuge etc.) allow a coating process that yields a 400-500 micron-thick layer of fibrin that entraps bioactive components such platelets and WBCs, but is deprived of RBCs.

In order to assure the effectiveness of the procedure and the bioactivity of the coated implant, designed to be implanted immediately following coating, the CGF coating is further characterized. The potential of growth, prolifera- tion, migration, and differentiation of MSCs seeded onto CGF coating layer is studied. MSCs migration is assessed using the Boyden chamber assay.

FIGS. 14A and 14B illustrate a Boyden chamber to assess the effect of CGF-coated implants on MSC migration and growth rate. FIG. 14A illustrates the effect of growth factors released from CGF-coated implants on MSCs migration. FIG. 14B illustrates the effect of growth factors released from CGF-coated implants on MSCs growth rate.

Cells are placed in the cell culture insert or the upper chamber, separated by a porous membrane from the lower chamber, which contains the CGF-coated implant. The cells and the implant are submerged in a shared serum-free medium. The cells are then allowed to migrate from the upper chamber to the underside surface of the insert, over 4 hours under incubated conditions. The cells on the upper membrane surface of the insert are then mechanically removed, and the migrated cells on the underside surface of the insert are fixed, stained and counted. This technique enables assessment of the percentage of MSCs migration toward growth factors released from CGF-coated implant. The effect of these factors on the growth rate of MSCs in the lower chamber in the presence versus absence of CGF- coated implants in the upper chamber can also be assessed and compared over time (FIG. 14B). The expression of osteogenic genes in MSCs seeded onto CGF coating layer is determined using techniques such as FACS and real-time PCR. The osteogenic potential of MSCs seeded onto the CGF coating layer is tested in vitro using alkaline phos- phatase activity assays and assessment of mineralization of cells.

Mini and standard implants with the appropriate contain- ers for CGF coating are used for proof of concept studies to verify acceleration of osseointegration following placement of CGF-coated implants in bone tissue of rat tibia. Standard- size implants are also tested in humans, along with the appropriate container for CGF coating. These coated implants are placed in bone tissue of the dog mandible, to establish clinical protocol for human patients.

Following in vitro studies characterizing MSC differen- tiation in the presence of the CGF coating, feasibility studies are conducted, in which CGF-coated implants are trans- planted into an the rat tibia to test their osseointegration rate within bone tissue. Wistar nude rats are anesthetized and an incision is made over the right anterior-proximal tibia sur- face. Care is taken to preserve the periosteal surface. Holes are drilled through one cortex, using a 1 mm drill bit and implants are placed. The skin is closed around the implant with non-absorbable sutures and pain is managed. Two groups of animal are tested and compared, i.e., those receiv- ing the CGF-coated implants versus those receiving the non-coated implants. The CGF coating procedure is per- formed with human blood. Implant osseointegration is assessed at various time points (e.g., 2, 4, 6, and 10 weeks after installing implants). A total of 40 rats is needed for the study. At the end of experiment, rats are anesthetized; the tibia bone in which implants are installed is excised, fixed in formalin, and embedded in paraffin for histological analysis, or analyzed with an ex vivo micro-CT scanners to assess bone tissue formation or implant osseointegration. Rats are sacrificed by intracardiac administration of pentobarbital sodium salt.

Osseointegration of CGF-coated implants is evaluated in a canine model. Two groups comprised of four male beagle dogs each, approximately two years old and weighing 15-18 kg, are radiographically screened before tooth extraction to rule out any pathology. Two mandibular implants are implanted in each dog, with one group receiving CGF- coated implants and the other receiving bare implants. CGF implant coating is performed with autologous blood, col- lected from the dog being treated. Dogs undergo surgery under halothane gas anesthesia. Heart rate, temperature, and respiration rate are monitored during surgery. The edentu- lation procedure of dogs is assessed radiographically. Venous blood of the dogs is used for implant coating. Osseointegration and bone tissue healing around the implants is radiographically assessed at 1, 3, 6 months post-implantation. At the 6 month time point, implants are also histologically evaluated. Histomorphometric analysis is conducted to determine the percent bone contact length along the implant.

FIG. 15 schematically illustrates, another exemplary embodiment of the device 1 configured to form a putty bone from a bone material, for example bone substitute. A bone material 600, in the form of powder, fragments, and the like, is placed within a vacuumed container 10. The container 10 is provided with a fixed separator 40 that separates the container to two parts, a bottom part and an upper part. The separator 40 is provided with holes so that when the container 10 is filled with whole blood 500, the blood 500 in the bottom part of the container 10 is in full contact with the blood 500 in the upper part of the container 10. The bone material 600 is in the upper part of the container 10, on top of the separator 40. After the vacuum in the container 10 is replaced with a patient's blood 500, the container 10 is centrifuged in similar conditions as mentioned herein above. As a result of the centrifugation, the blood 500 is separated to a bottom phase 510 comprising red blood cells and platelets, mostly concentrated in the bottom part of the container 10, under the separator 40, and an upper phase 520 comprising plasma in the upper part of the container 10, above the separator 40. Again, the plasma contains osseointegration accelerators that adhere to the bone material 600 so as to form a putty bone 700, ready to be used.

FIG. 16 schematically illustrates, according to an exemplary embodiment, a disassembled device 1 configured to form a putty bone from a bone material. The container 10, exemplary components of the cover 20 and the separator 40 are illustrated.

FIG. 17 schematically illustrates, according to an exemplary embodiment, an assembled device 1 configured to form a putty bone from a bone material. The container 10, exemplary components of the cover 20 and the separator 40 are illustrated.

FIG. 18. schematically illustrates, according to an exemplary embodiment, a system for withdrawing whole blood from a vein directly from a vein of a patient into a device 1 configured to form a putty bone from a bone material. The components of the system are as described in FIG. 2, and the device 1 configured to form a putty bone from a bone material is as described in FIG. 15.

FIGS. 19A-19I are SEM images of a putty bone 700 prepared by using the device 1 configured to form a putty bone from a bone material.

It is appreciated that certain features of the subject matter, which are, for clarity, described in the context of separate embodiments, may also be provided in combination in a single embodiment. Conversely, various features of the subject matter, which are, for brevity, described in the context of a single embodiment, may also be provided separately or in any suitable sub combination.

Although the subject matter has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method for forming a putty bone from a bone material, the method comprising:

placing the bone material in a container having an opening and a cover for covering the opening, and a fixed separator that separates the container to a bottom part and an upper part, wherein the separator is provided with holes so that when the container is filled with whole blood, the whole blood in the bottom part is in full contact with the whole blood in the upper part, and wherein the bone material is in the upper part, on top of the separator;

filling the container with whole blood;

centrifuging the container in a manner that separates the whole blood to a bottom phase comprising red blood cells and platelets that are mostly concentrated in the bottom part, and an upper phase comprising plasma in the upper part, thus allowing the plasma to adhere to the bone material to form a putty bone.

2. The method of claim 1, wherein the container, when covered with the cover is configured to maintain a negative air pressure compared to an ambient air pressure, and the whole blood is withdrawn into the container due to the negative air pressure in the container.

3. The method of claim 1, wherein the bone material is bone substitute, in the form of powder or fragments.

* * * * *